(12) United States Patent
Speake et al.

(10) Patent No.: US 10,556,909 B2
(45) Date of Patent: Feb. 11, 2020

(54) SYNTHETIC PROCESS AND INTERMEDIATES

(71) Applicant: Avista Pharma Solutions, Inc., Durham, NC (US)

(72) Inventors: Jason D. Speake, Winston-Salem, NC (US); Bharathi Pandi, Cary, NC (US); Cyprian O. Ogbu, Durham, NC (US); Jeffrey A. Adams, Chapel Hill, NC (US); Joseph A. Moore, III, Wake Forest, NC (US); Joe B. Perales, Durham, NC (US); Keqiang Li, Cary, NC (US)

(73) Assignee: Avista Pharma Solutions, Inc., Durham, NC (US)

( * ) Notice: Subject to any disclaimer, the term of this patent is extended or adjusted under 35 U.S.C. 154(b) by 0 days.

(21) Appl. No.: 16/302,944

(22) PCT Filed: May 17, 2017

(86) PCT No.: PCT/US2017/033048
§ 371 (c)(1),
(2) Date: Nov. 19, 2018

(87) PCT Pub. No.: WO2017/201134
PCT Pub. Date: Nov. 23, 2017

(65) Prior Publication Data
US 2019/0284199 A1    Sep. 19, 2019

Related U.S. Application Data

(60) Provisional application No. 62/491,337, filed on Apr. 28, 2017, provisional application No. 62/339,136, filed on May 20, 2016.

(51) Int. Cl.
*C07D 491/107* (2006.01)
*A01N 43/90* (2006.01)

(52) U.S. Cl.
CPC ......... *C07D 491/107* (2013.01); *A01N 43/90* (2013.01)

(58) Field of Classification Search
CPC .................................................. C07D 491/107
See application file for complete search history.

(56) References Cited

U.S. PATENT DOCUMENTS

| 9,420,793 B2* | 8/2016 | Speake ................. A01N 43/90 |
| 2012/0232026 A1 | 9/2012 | Curtis et al. |
| 2015/0181882 A1 | 7/2015 | Menon et al. |
| 2015/0209355 A1 | 7/2015 | Chubb et al. |
| 2015/0210710 A1 | 7/2015 | Sheehan et al. |
| 2015/0291612 A1 | 10/2015 | Greenwood et al. |

FOREIGN PATENT DOCUMENTS

| WO | WO-2014039489 A1 * | 3/2014 | ........... C07D 491/10 |
| WO | 2015048371 A1 | 4/2015 | |

OTHER PUBLICATIONS

International Search Report, dated Aug. 24, 2017, for PCT/US17/33048 filed May 17 2017.
Pubmed Compound Summary for CID 66555339, U.S. National Library of Medicine, Nov. 5, 2012, https://pubchem.ncbi.nlm.nih.gov/compound/66555339; p. 3.
Pubmed Compound Summary for CID 89994605, SCHEMBL 15505713, U.S. National Library of Medicine, Feb. 13, 2015, https://pubchem.ncbi.nlm.nih.gov/compound/89994605; p. 4.
Pubmed Compound Summary for CID 89994583, SCHEMBL 15505679, U.S. National Library of Medicine, Feb. 13, 2015, https://pubchem.ncbi.nlm.nih.gov/compound/89994583; p. 4.

* cited by examiner

*Primary Examiner* — Laura L Stockton
(74) *Attorney, Agent, or Firm* — Barnes & Thornburg LLP

(57) ABSTRACT

The present disclosure describes a synthetic process and novel intermediates related to spirocyclic azetidenyl-isobenzofuran derivatives having an isothiazoline moiety, which are useful as antiparasitics.

20 Claims, No Drawings

SYNTHETIC PROCESS AND INTERMEDIATES

CROSS-REFERENCE TO RELATED APPLICATION

This application is a National Stage application of International Application No. PCT/US2017/033048, filed May 17, 2017, which claims the benefit of U.S. Provisional Application No. 62/491,337, filed Apr. 28, 2017 and U.S. Provisional Application No. 62/339,136 filed May 20, 2016.

FIELD

The present disclosure describes a synthetic process and novel intermediates related to spirocyclic azetidenyl-isobenzofuran derivatives having an isothiazoline moiety, which are useful as antiparasitics.

BACKGROUND

There is a need for improved antiparasitics, and in particular there is a need for improved insecticides and acaricides, particularly for use in animal health. Furthermore, there is a need for improved topical and oral products with convenient administration. Still further, there is a need for improved compositions which contains one or more active antiparasitics, which can be used to effectively treat against parasites. Such improvements would be particularly useful for the treatment of animals including: birds (e.g., chickens and turkeys), fish, companion animals (e.g., cats, dogs, llamas, and horses), and livestock (e.g., cattle, bison, swine, sheep, deer, elk, and goats).

Currently available insecticidal and acaricidal treatments for animals do not always demonstrate good activity, good speed of action, or a long duration of action. Most treatments contain hazardous chemicals that can have serious consequences, including neurotoxicity and lethality from accidental ingestion. Persons applying these agents are generally advised to limit their exposure. Pet collars and tags have been utilized to overcome some problems, but these are susceptible to chewing, ingestion, and subsequent toxicological effects to the animal. Thus, current treatments achieve varying degrees of success, which depend partly on toxicity, method of administration, and efficacy. Additionally, some currently available agents are becoming ineffective due to parasitic resistance.

Despite the availability of effective, broad spectrum antiparasitics, there remains a need for safer and more convenient, efficacious, and environmentally friendly products that will overcome the ever-present threat of resistance development.

PCT/US2016/013358, herein incorporated by reference in its entirety, describes isothiazoline spiroazetidinyl-isobenzofuran derivatives which are demonstrated to be effective, broad spectrum antiparasitics. More specifically, the isothiazoline spiroazetidinyl isobenzofuran derivatives, including pesticidal, veterinary, or pharmaceutically acceptable salts thereof, are represented by Formula (I):

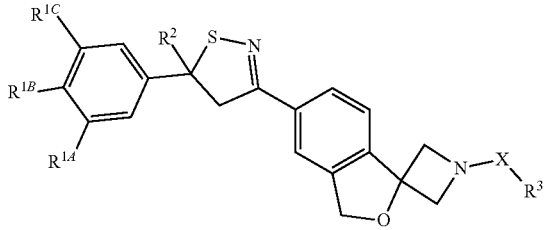

Formula (I)

wherein each $R^{1A}$, $R^{1B}$, and $R^{1C}$ individually is hydrogen, alkyl, halogen, or haloalkyl; $R^2$ is haloalkyl; X is bond, C(O), SO$_2$, or C(O)NH; $R^3$ is hydrogen, optionally substituted alkyl, optionally substituted haloalkyl, optionally substituted cycloalkyl, optionally substituted heterocyclyl, optionally substituted aryl, and optionally substituted heteroaryl, or a pesticidal, veterinary, or pharmaceutically acceptable salt thereof. One embodiment described is a compound 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one, or a pesticidal, veterinary, or pharmaceutically acceptable salt thereof.

SUMMARY

The present disclosure describes a synthetic process for the compounds of Formula (I) of PCT/US2016/013358, in particular for the compound 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one, or a pesticidal, veterinary, or pharmaceutically acceptable salt thereof.

The compound, 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one, is referred to herein as Compound A, and may also be referred to as 1-(5'-(5-(3,5-dichloro-4-fluorophenyl)-5-(trifluoromethyl)-4,5-dihydroisothiazol-3-yl)-3'H-spiro[azetidine-3,1'-isobenzofuran]-1-yl)-3,3,3-trifluoropropan-1-one, depending on naming convention. Compound A is a useful antiparasitic compound, particularly as a flea and/or tick infestation treatment or preventative.

The preparation of Compound A or a veterinary acceptable salt thereof may be accomplished via the route and novel intermediates herein described.

One embodiment of the present disclosure is a compound 1-(6-bromospiro[1H-isobenzofuran-3,3'azetidine]-1'-yl)-3,3,3-trifluoro-propane-1-one, which may be referred to as 1-(5'-bromo-3'H-spiro[azetidine-3,1'-isobenzofuran]-1-yl)-3,3,3-trifluoropropan-1-one, depending on naming convention.

Another embodiment of the present disclosure is a process for making 1-(6-bromospiro[1H-isobenzofuran-3,3'azetidine]-1'-yl)-3,3,3-trifluoro-propane-1-one comprising: acylating an azetidone, such as 3-azetidinone or a salt thereof, with 3,3,3-trifluoroprionyl chloride; and spirocyclizing using 4-bromo-2-(chloromethyl)-1-iodo-benzene.

Another embodiment of the present disclosure is a process for making 1-(6-bromospiro[1H-isobenzofuran-3,3'azetidine]-1'-yl)-3,3,3-trifluoro-propane-1-one comprising: protecting azetidinone hydrochloride with a protecting group, such as a phenyl carbamate protecting group; spirocyclizing, for example using 4-bromo-2-(chloromethyl)-1-iodo-benzene; removing the protecting group; and acylating using 3,3,3-trifluoroprionyl chloride. The spirocyclization step may use an anhydrous lanthanide salt.

Another embodiment of the present disclosure is a process for making 1-(6-bromospiro[1H-isobenzofuran-3,3'azetidine]-1'-yl)-3,3,3-trifluoro-propane-1-one without the use of an azetidinone reagent. Rather, a dioxanone is used to spirocyclize 4-bromo-2-(chloromethyl)-1-iodo-benzene, followed by opening the dioxane ring to a di-alcohol, converting to a di-nitrobenzenesulfonate, and subsequently closing the ring to form an spiroazetidine moiety.

Another embodiment of the present disclosure is a compound 3-(3,5-dichloro-4-fluoro-phenyl)-4,4,4-trifluoro-1-[1'-(3,3,3-trifluoropropanoyl)spiro[3H-isobenzofuran-1,3'-azetidine]-5-yl]but-2-en-1-one.

Another embodiment of the present disclosure is a compound 3-(3,5-dichloro-4-fluoro-phenyl)-4,4,4-trifluoro-3-sulfanyl-1-[1'-(3,3,3-trifluoropropanoyl)spiro[3H-isobenzofuran-1,3'-azetidine]-5-yl]butan-1-one.

Another embodiment of the present disclosure is a process for making 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one or salt thereof comprising: forming an isothiazoline ring by treating 3-(3,5-dichloro-4-fluoro-phenyl)-4,4,4-trifluoro-3-sulfanyl-1-[1'-(3,3,3-trifluoropropanoyl)spiro[3H-isobenzofuran-1, 3'-azetidine]-5-yl]butan-1-one with hydroxylamine-O-sulfonic acid.

Another embodiment of the present disclosure is a process for making 1-[6-[5-(3,5-dichloro-4-fluoro-phenyl)-5-(trifluoromethyl)-4H-isothiazol-3-yl]spiro[1H-isobenzofuran-3, 3'-azetidine]-1'-yl]-3,3,3-trifluoro-propan-1-one or salt thereof comprising: converting 1-(6-bromospiro[1H-isobenzofuran-3,3'azetidine]-1'-yl)-3,3,3-trifluoro-propane-1-one to an acetophenone derivative using a palladium coupling with n-butyl vinyl ether; reacting the acetophenone derivative with 1-(3,5-dichloro-4-fluoro-phenyl)-2,2,2-trifluoroethanone to form an enone derivative; treating the enone derivative with sodium thiolate to form a sulfanyl derivative; and reacting the sulfanyl derivative with hydroxylamine-O-sulfonic acid to form 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one or salt thereof.

Another embodiment of the present disclosure is a compound of Formula (I)

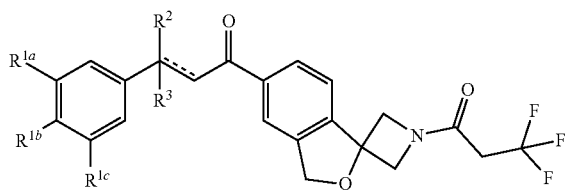

Formula (I)

wherein
each of $R^{1a}$, $R^{1b}$, and $R^{1c}$ individually is a halogen;
$R^2$ is a $C_{1-6}$ haloalkyl;
the depicted dashed bond is absent or the depicted dashed bond is present to form a double bond; and
$R^3$ is SH if the depicted dashed bond is absent.

One aspect of the embodiment includes wherein $R^{1a}$ is Cl; $R^{1b}$ is F; $R^{1c}$ is Cl; $R^2$ is $CF_3$; and the depicted dashed bond is present to form a double bond. One aspect of the embodiment includes wherein $R^{1a}$ is Cl; $R^{1b}$ is F; $R^{1c}$ is Cl; $R^2$ is $CF_3$; the depicted dashed bond is absent; and $R^3$ is SH.

Another embodiment of the present disclosure is a process for making 1-[6-[5-(3,5-dichloro-4-fluoro-phenyl)-5-(trifluoromethyl)-4H-isothiazol-3-yl]spiro[1H-isobenzofuran-3, 3'-azetidine]-1'-yl]-3,3,3-trifluoro-propan-1-one or salt thereof comprising using 1-(6-bromospiro[1H-isobenzofuran-3,3'azetidine]-1'-yl)-3,3,3-trifluoro-propane-1-one.

Another embodiment of the present disclosure is a process for making 1-[6-[5-(3,5-dichloro-4-fluoro-phenyl)-5-(trifluoromethyl)-4H-isothiazol-3-yl]spiro[1H-isobenzofuran-3, 3'-azetidine]-1'-yl]-3,3,3-trifluoro-propan-1-one or salt thereof comprising using 3-(3,5-dichloro-4-fluoro-phenyl)-4,4,4-trifluoro-1-[1'-(3,3,3-trifluoropropanoyl)spiro[3H-isobenzofuran-1,3'-azetidine]-5-yl]but-2-en-1-one.

Another embodiment of the present disclosure is a process for making 1-[6-[5-(3,5-dichloro-4-fluoro-phenyl)-5-(trifluoromethyl)-4H-isothiazol-3-yl]spiro[1H-isobenzofuran-3, 3'-azetidine]-1'-yl]-3,3,3-trifluoro-propan-1-one or salt thereof comprising using 3-(3,5-dichloro-4-fluoro-phenyl)-4,4,4-trifluoro-3-sulfanyl-1-[1'-(3,3,3-trifluoropropanoyl) spiro[3H-isobenzofuran-1,3'-azetidine]-5-yl]butan-1-one.

Another embodiment of the present disclosure is a process for making (+)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one or a salt thereof which is enantiomerically enriched from (−)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one or a salt thereof.

In one embodiment, the enantiomeric enrichment ratio is approximately 94:6. In one embodiment, the enantiomeric enrichment ratio is 95:5. In one embodiment, the enantiomeric enrichment ratio is 96:4. In one embodiment, the enantiomeric enrichment ratio is 97:3. In one embodiment, the enantiomeric enrichment ratio is 98:2. In one embodiment, the enantiomeric enrichment ratio is 99:1. In one embodiment, the enantiomeric enrichment ratio is 100:0.

DETAILED DESCRIPTION

One or more aspects and embodiments may be incorporated in a different embodiment although not specifically described. That is, all aspects and embodiments can be combined in any way or combination.

The present disclosure describes a synthetic process for the compound 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one, or a pesticidal, veterinary, or pharmaceutically acceptable salt thereof, referred to herein as Compound A, which is a useful anti-parasitic compound, particularly as a flea and/or tick infestation treatment or preventative.

The preparation of Compound A or a veterinary acceptable salt thereof may be accomplished via the route and novel intermediates shown hereinbelow.

Preparation of 1-(6-bromospiro[1H-isobenzofuran-3,3'-azetidine]-1'-yl)-3,3,3-trifluoro-propan-1-one (Intermediate Compound 1), which also may be referred to as 1-(5'-bromo-3'H-spiro[azetidine-3,1'-isobenzofurn]-1-yl)-3,3,3-trifluoropropan-1-one, depending upon the naming convention used, may be achieved by acylation of azetidinone with trifluoroprionylchloride, followed by a spirocyclization reaction as shown in Scheme 1A.

SCHEME 1A

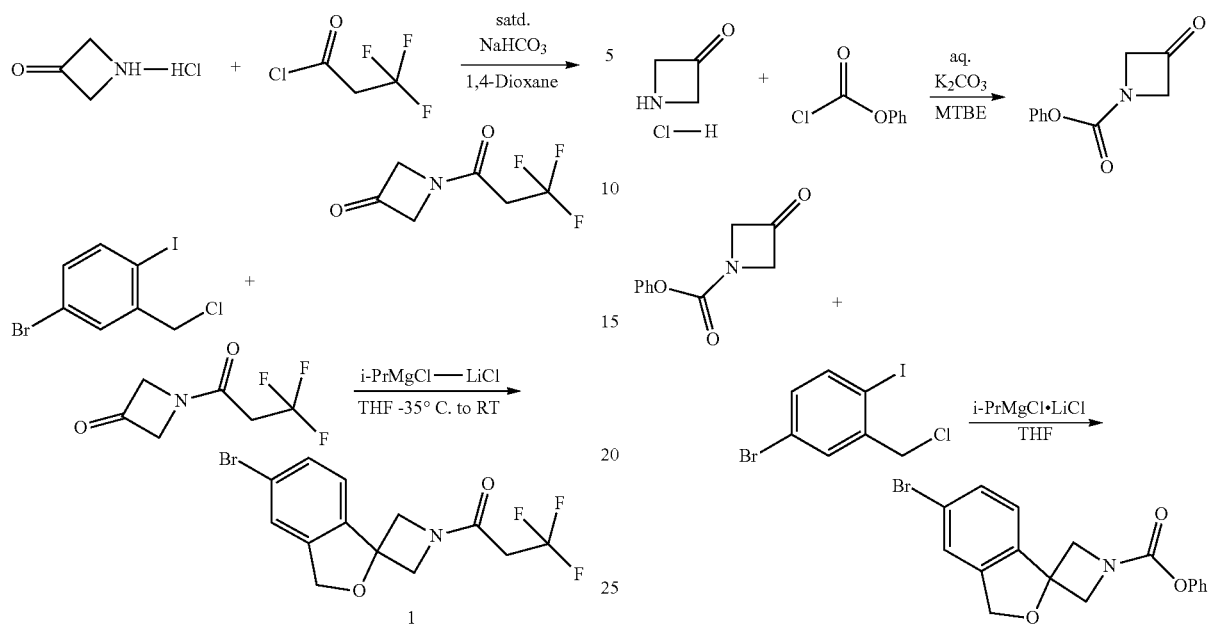

The present invention includes an alternative method including an anhydrous lanthanide salt in the spirocyclization step, shown in Scheme 1B.

SCHEME 1B

SCHEME 1C

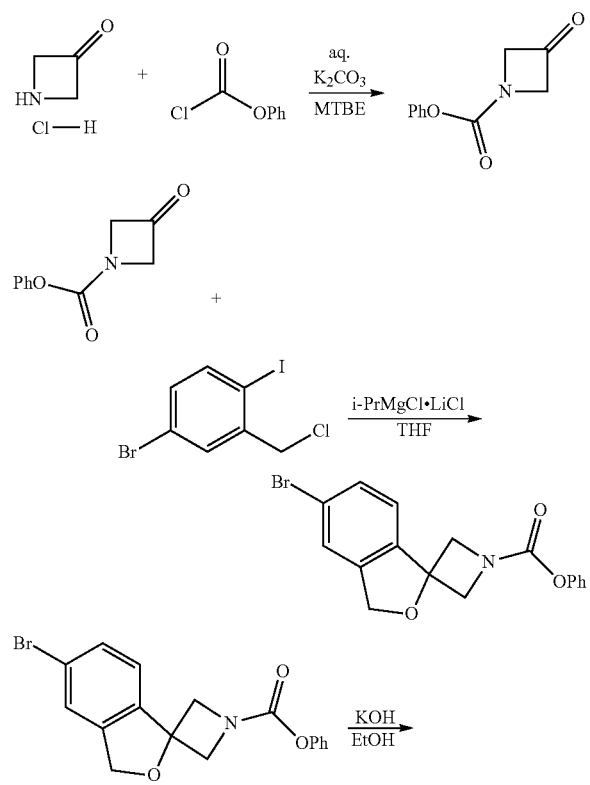

The present invention includes an alternate method including a phenyl carbamate protecting group followed by deprotection and reacylation, as shown in Scheme 1C.

Alternatively, this intermediate can be prepared through a similar sequence involving a protecting group, spirocyclization, deprotection, and reacylation with alternative reagents and conditions as shown in Scheme 1D.

SCHEME 1D

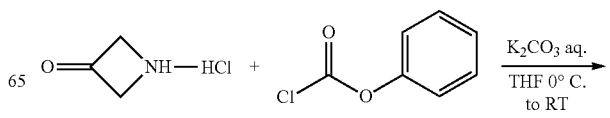

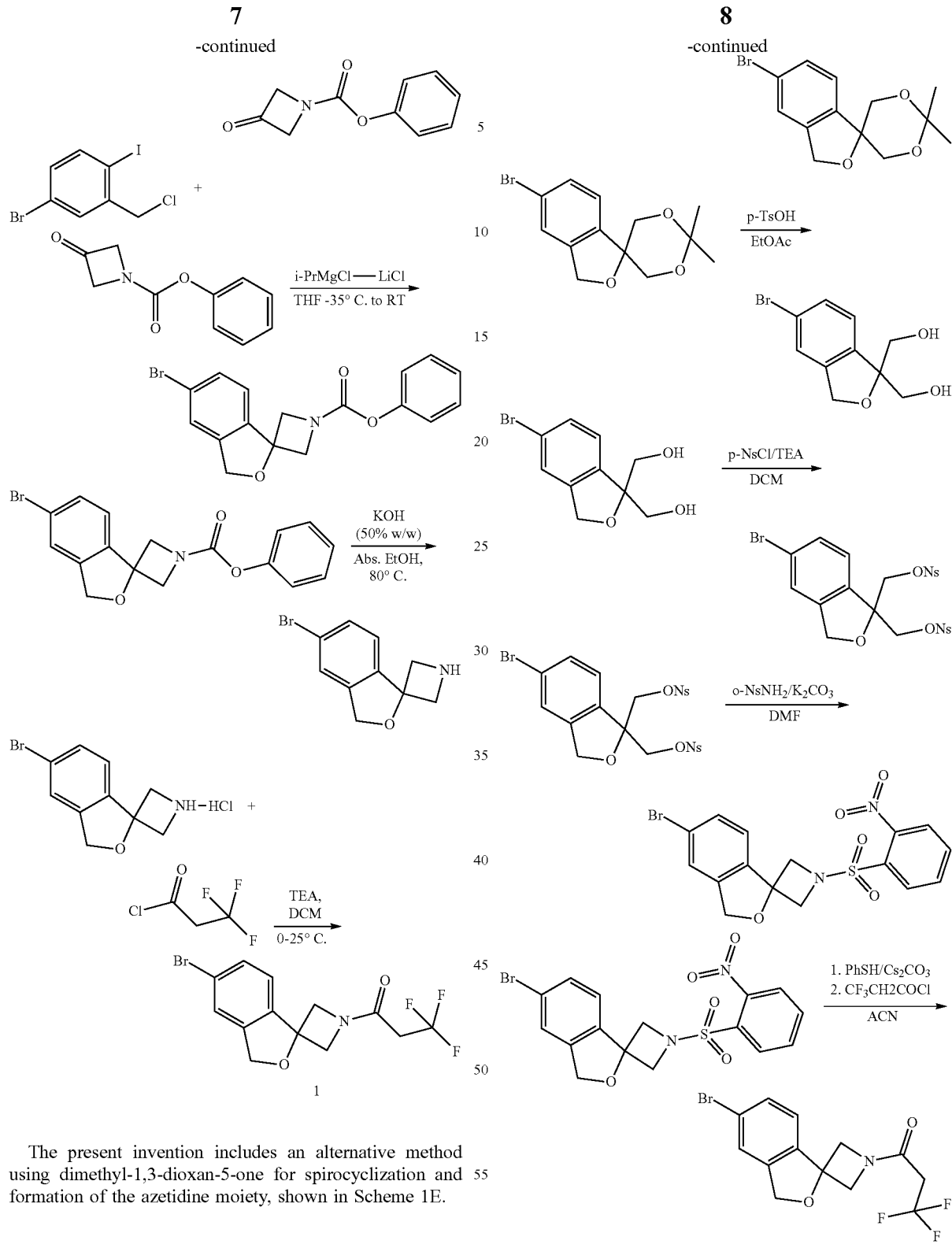

The present invention includes an alternative method using dimethyl-1,3-dioxan-5-one for spirocyclization and formation of the azetidine moiety, shown in Scheme 1E.

SCHEME 1E

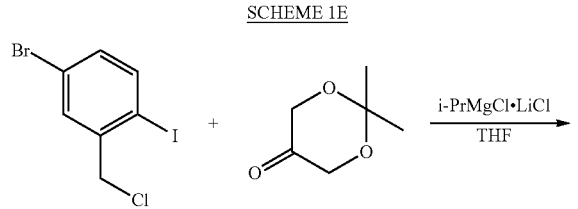

Conversion of Intermediate Compound 1 to the desired 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one, involves the multistep sequence shown in Scheme 3. As will be detailed therein, preparation reagent 1-(3,5-dichloro-4-fluorophenyl)-2,2,2- trifluoroethan-1-one (herein also referred to as Intermediate Compound 9) may be prepared via Grignard, namely by contacting 1-bromo-3,5-dichloro-4-fluorobenzene with methyl trifluoroacetate and an alkylmagnesium halide, as shown in Scheme 2.

SCHEME 2

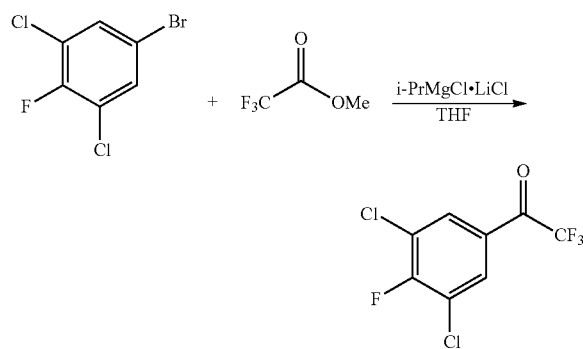

Thus, as set forth in Scheme 3A, conversion of the bromide of Intermediate Compound 1 to an acetophenone derivative using a palladium coupling with n-butyl vinyl ether and reaction with Intermediate Compound 9 provides the enone intermediate 3-(3,5-dichloro-4-fluoro-phenyl)-4,4,4-trifluoro-1-[1'-(3,3,3-trifluoropropanoyl)spiro[3H-isobenzofuran-1,3'-azetidine]-5-yl]but-2-en-1-one.

Formation of the isothiazoline ring is then accomplished by treatment of the enone with sodium thiolate followed by hydroxylamine-O-sulfonic acid.

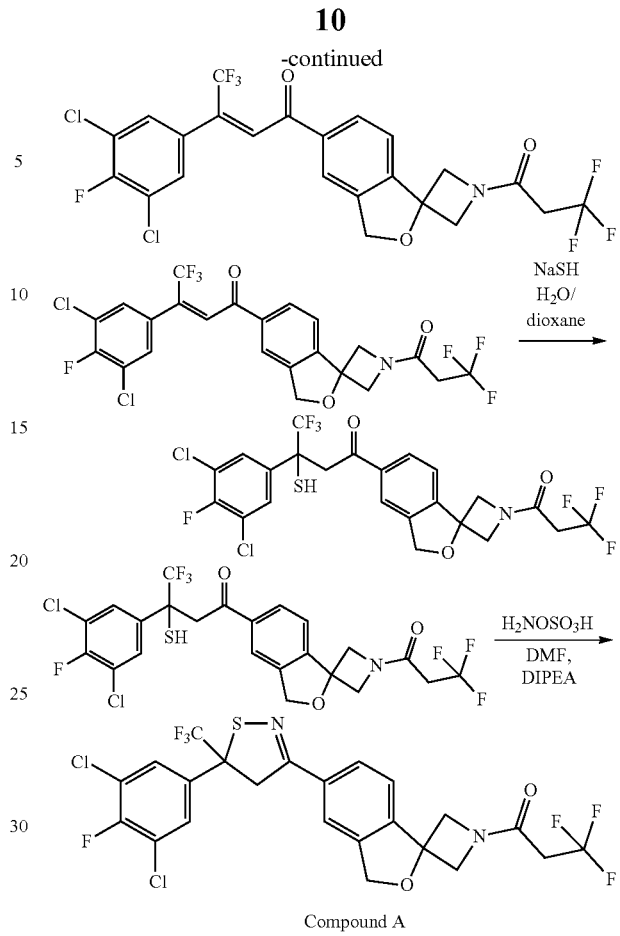

Compound A

The present invention includes an alternative method, with alternative reagents and conditions, as shown in Scheme 3B.

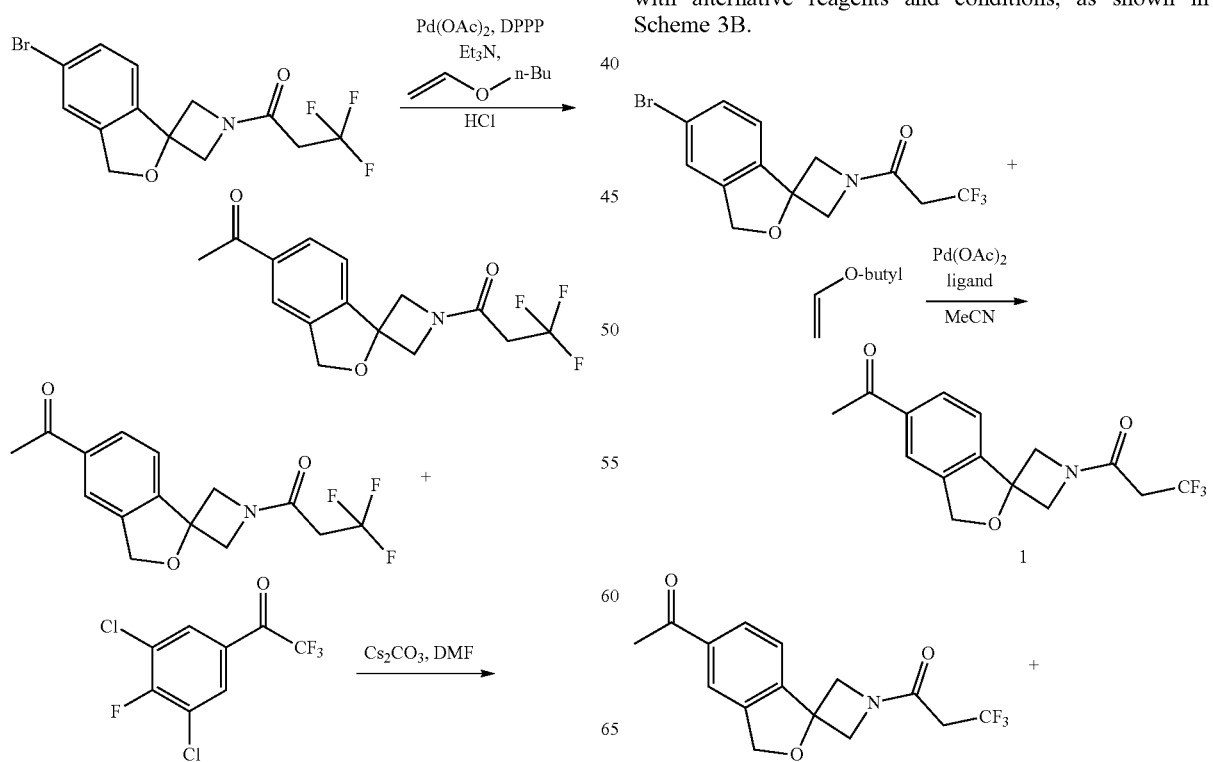

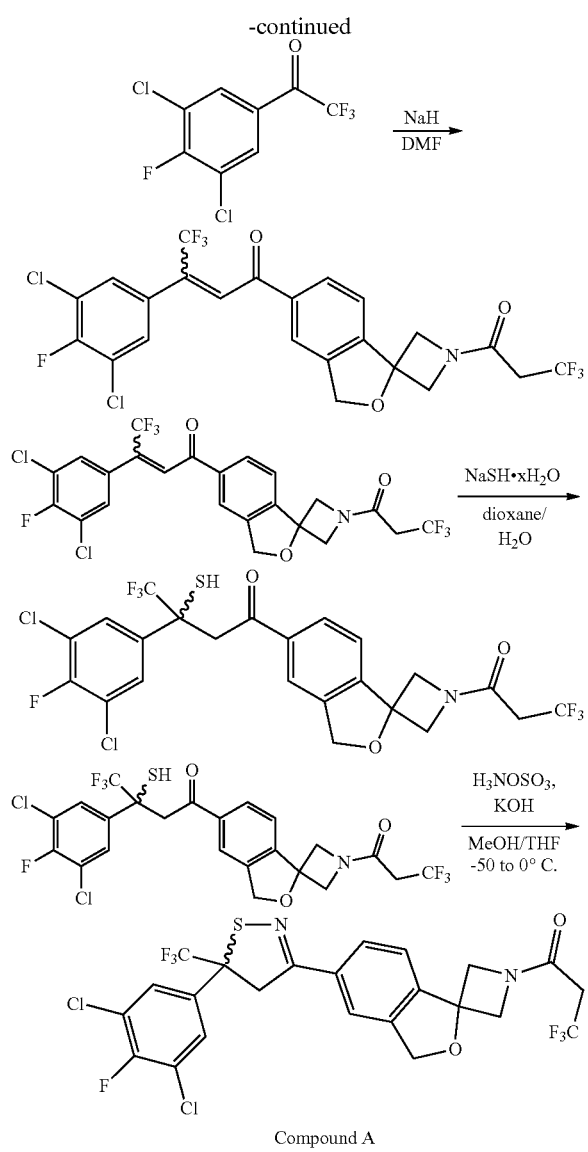

Compound A

As used herein the phrase pesticidal or pesticidally, veterinary or veterinarily, or pharmaceutical or pharmaceutically acceptable salt refers to any salt of a compound disclosed herein which retains its biological properties and which is not toxic or otherwise undesirable for pesticidal, veterinary, or pharmaceutical use. Certain compounds of the present invention have sites that would allow for a pesticidal or pesticidally, veterinary or veterinarily, or pharmaceutical or pharmaceutically acceptable salt, and such salt forms are also included in the present invention. Such salts may be derived from a variety of organic and inorganic counter-ions known in the art. Such salts include: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid, and like acids.

Salts further include, by way of example only, salts of non-toxic organic or inorganic acids, such as halides, such as, chloride and bromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate, and the like.

As used herein, the terms "subject" and "patient" are used interchangeably herein. The terms "subject" and "subjects" refer to a primate such as a monkey such as a cynomolgus monkey, a chimpanzee, and a human or non-primate animal. In one embodiment, the subject is a human. In another embodiment, the subject is a companion animal such as a dog or cat. In a further embodiment, the subject is an animal of agricultural importance such as a sheep, cow, horse, goat, fish, pig, or domestic fowl (such as a chicken, turkey, duck, or goose).

In addition, certain compounds of the present invention have substituent groups that would allow for a pharmaceutically acceptable prodrug moiety, and such prodrug forms are also included in the present invention. A pharmaceutically acceptable prodrug refers to a compound having a group which can be converted into an amino group, a hydroxyl group, a carboxyl group, or the like, by solvolysis or under a physiological condition. Examples of the groups forming the prodrug include those as described in Prog. Med., 5, 2157-2161 (1985) or "Pharmaceutical Research and Development" (Hirokawa Publishing Company, 1990), vol. 7, Drug Design, 163-198. The term prodrug is used throughout the specification to describe any pharmaceutically acceptable form of a compound which, upon administration to a patient, provides the active compound. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

The present invention includes all pharmaceutically acceptable isotopically-labelled compounds of the invention wherein one or more atoms are replaced by atoms having the same atomic number, but an atomic mass or mass number different from the atomic mass or mass number usually found in nature. Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}$O, $^{17}$O and $^{18}$O, phosphorus, such as $^{32}$P, and sulfur, such as $^{35}$S. Certain isotopically-labelled compounds of the invention, such as those incorporating a radioactive isotope, may be useful in drug or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labelled compounds of the invention can generally be prepared by conventional techniques known to those skilled in the art or by processes analogous to those described in the accompanying Examples and Preparations using an appropriate isotopically-labelled reagents in place of the non-labelled reagent previously employed.

Compositions and Methods of Administration

Compound A or a veterinary acceptable salt thereof, made in the methods disclosed herein, can be administered in certain embodiments using veterinary, pharmaceutical, or pesticidal compositions including at least one compound of formula (I), if appropriate in the salt form, either used alone or in the form of a combination with one or more compatible and veterinarily, pharmaceutically, or pesticidally acceptable carriers, such as diluents or adjuvants, or with another agent. There are provided compositions which comprise Compound A or a veterinary acceptable salt thereof, and an acceptable excipient, carrier or diluent. The composition can also be in a variety of forms which include, but are not limited to, oral formulations, injectable formulations, and topical, dermal or subdermal formulations.

The composition can be in a form suitable for oral use, for example, as dietary supplements, troches, lozenges, chewables, tablets, hard or soft capsules, emulsions, aqueous or oily suspensions, aqueous or oily solutions, dispersible powders or granules, syrups, or elixirs. Compositions intended for oral use can be prepared according to any method known in the art for the manufacture of veterinary, pharmaceutical, or pesticidal compositions and such compositions can contain one or more agents selected from the group consisting of sweetening agents, bittering agents, flavoring agents, coloring agents and preserving agents in order to provide elegant and palatable preparations.

Tablets can contain the active ingredient in admixture with non-toxic, pharmaceutically acceptable excipients which are suitable for the manufacture of tablets. These excipients can be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period.

Formulations for oral use can be hard gelatin capsules, wherein the active ingredient is mixed with an inert solid diluent, for example, calcium carbonate, calcium phosphate or kaolin. Capsules can also be soft gelatin capsules, wherein the active ingredient is mixed with water or miscible solvents such as propylene glycol, PEGs and ethanol, or an oil medium, for example, peanut oil, liquid paraffin, or olive oil.

The compositions can also be in the form of oil-in-water or water-in-oil emulsions. The oily phase can be a vegetable oil, for example, olive oil or arachis oil, or a mineral oil, for example, liquid paraffin or mixtures of these. Suitable emulsifying agents may be naturally-occurring phosphatides, for example, soy bean, lecithin, and esters or partial esters derived from fatty acids and hexitol anhydrides, for example, sorbitan monoleate, and condensation products of the said partial esters with ethylene oxide, for example, polyoxyethylene sorbitan monooleate. The emulsions can also contain sweetening agents, bittering agents, flavoring agents, and preservatives.

In one embodiment of the formulation, the composition is in the form of a microemulsion. Microemulsions are well suited as the liquid carrier vehicle. Microemulsions are quaternary systems comprising an aqueous phase, an oily phase, a surfactant and a cosurfactant. They are translucent and isotropic liquids. Microemulsions are composed of stable dispersions of microdroplets of the aqueous phase in the oily phase or conversely of microdroplets of the oily phase in the aqueous phase. The size of these microdroplets is less than 200 nm (1000 to 100,000 nm for emulsions). The interfacial film is composed of an alternation of surface-active (SA) and co-surface-active (Co-SA) molecules which, by lowering the interfacial tension, allows the microemulsion to be formed spontaneously. In one embodiment of the oily phase, the oily phase can be formed from mineral or vegetable oils, from unsaturated polyglycosylated glycerides or from triglycerides, or alternatively from mixtures of such compounds. In one embodiment of the oily phase, the oily phase comprises of triglycerides; in another embodiment of the oily phase, the triglycerides are medium-chain triglycerides, for example, $C_8$-$C_{10}$ caprylic/capric triglyceride. In another embodiment, the oily phase will represent a % v/v range selected from the group consisting of about 2 to about 15%; about 7 to about 10%; and about 8 to about 9% v/v of the microemulsion. The aqueous phase includes, for example, water or glycol derivatives, such as propylene glycol, glycol ethers, polyethylene glycols or glycerol. In one embodiment of the glycol derivatives, the glycol is selected from the group consisting of propylene glycol, diethylene glycol monoethyl ether, dipropylene glycol monoethyl ether and mixtures thereof. Generally, the aqueous phase will represent a proportion from about 1 to about 4% v/v in the microemulsion. Surfactants for the microemulsion include diethylene glycol monoethyl ether, dipropylene glycol monomethyl ether, polyglycolyzed $C_8$-$C_{10}$ glycerides or polyglyceryl-6 dioleate. In addition to these surfactants, the cosurfactants include short-chain alcohols, such as ethanol and propanol. Some compounds are common to the three components discussed above, for example, aqueous phase, surfactant and cosurfactant. However, it is well within the skill level of the practitioner to use different compounds for each component of the same formulation. In one embodiment for the amount of surfactant/cosurfactant, the cosurfactant to surfactant ratio will be from about ½ to about ½.

In another embodiment for the amount of cosurfactant, there will be from about 25 to about 75% v/v of surfactant and from about 10 to about 55% v/v of cosurfactant in the microemulsion.

Oily suspensions can be formulated by suspending the active ingredient in a vegetable oil, for example, atachis oil, olive oil, sesame oil or coconut oil, or in mineral oil such as liquid paraffin. The oily suspensions can contain a thickening agent, for example, beeswax, hard paraffin or cetyl alcohol. Sweetening agents such as sucrose, saccharin or aspartame, bittering agents, and flavoring agents can be added to provide a palatable oral preparation. These compositions can be preserved by the addition of an anti-oxidant such as ascorbic acid, or other known preservatives.

Aqueous suspensions can contain the active material in admixture with excipients suitable for the manufacture of aqueous suspensions. Such excipients are suspending agents, for example, sodium carboxymethylcellulose, methylcellulose, hydroxypropylmethylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example, polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example, polyethylene sorbitan monooleate. The aqueous suspensions can also contain one or more preservatives, for example, ethyl, or n-propyl, p-hydroxybenzoate, one or more coloring agents, one or more flavoring agents, and one or more sweetening agents and/or bittering agents, such as those set forth above.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, bittering, flavoring and coloring agents, can also be present.

Syrups and elixirs can be formulated with sweetening agents, for example, glycerol, propylene glycol, sorbitol or sucrose. Such formulations may also contain a demulcent, a preservative, flavoring agent(s), and coloring agent(s).

The compositions can be in the form of a sterile injectable aqueous or oleagenous suspension. This suspension can be formulated according to the known art using those suitable dispersing or wetting agents and suspending agents which have been mentioned above. The sterile injectable preparation can also be a sterile injectable solution or suspension in a non-toxic parenterally-acceptable diluent or solvent, for example, as a solution in 1,3-butane diol. Among the acceptable vehicles and solvents that can be employed are water, Ringer's solution and isotonic sodium chloride solution. Co-solvents such as ethanol, propylene glycol or polyethylene glycols can also be used. Preservatives, such as phenol or benzyl alcohol, can be used.

In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

Topical, dermal and subdermal formulations can include emulsions, creams, ointments, gels or pastes.

Organic solvents that can be used in the invention include but are not limited to: acetyltributyl citrate, fatty acid esters such as the dimethyl ester, diisobutyl adipate, acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone (e.g. N-methylpyrrolidone), diethylene glycol monoethyl ether, ethylene glycol and diethyl phthalate, or a mixture of at least two of these solvents.

As vehicle or diluent, compositions of the present invention may include plant oils such as, but not limited to soybean oil, groundnut oil, castor oil, corn oil, cotton oil, olive oil, grape seed oil, sunflower oil, etc.; mineral oils such as, but not limited to, petrolatum, paraffin, silicone, etc.; aliphatic or cyclic hydrocarbons or alternatively, for example, medium-chain (such as $C_8$-$C_{12}$) triglycerides.

Dosage forms can contain from about 0.5 mg to about 5 g of an active agent.

In one embodiment of the invention, the active agent is present in the formulation at a concentration of about 0.05 to 10% weight/volume.

The compounds of formula (I) can be employed as such or in the form of their preparations or formulations as combinations with other pesticidal active substances, such as, for example, insecticides, attractants, sterilants, nematicides, acaricides, fungicides, herbicides, and with safeners, fertilizers and/or growth regulators.

The compounds of formula (I) according to the invention may be combined with one or more agents having the same sphere of activity, for example, to increase activity, or with substances having another sphere of activity, for example, to broaden the range of activity. The compounds of the present invention may also be combined with so-called repellents. By combining the compounds of the formula I with other suitable parasiticides, not only the parasiticidal activity can be enhanced, but the greatest part of those parasites that produce great economic damage will be covered. Moreover, this action will contribute substantially to avoiding the formation of resistance. Preferred groups of combination partners and especially preferred combination partners are named in the following, whereby combinations may contain one or more of these partners in addition to a compound of formula I. Suitable partners may also be afoxolaner, sarolaner, fluralaner, or a combination thereof. Any of the individually listed agents can be used in combination with compounds of formula (I) along with any other one or more listed agents independently.

Suitable partners in the mixture may be biocides, namely insecticides and acaricides with a varying mechanism of activity, for example, chitin synthesis inhibitors, growth regulators, active ingredients which act as juvenile hormones, active ingredients which act as adulticides, broadband insecticides, broadband acaricides and nematicides, and also anthelminthics and insect- and acarid-deterring substances, repellents or detachers. Non-limiting examples of suitable insecticides and acaricides are:

1. Abamectin
2. Acephate
3. Acequinocyl
4. Acetamiprid
5. Acetoprole
6. Acrinathrin
7. AKD-1022
8. Alanycarb
9. Aldicarb
10. Aldoxycarb
11. Allethrin
12. Alpha-cypermethrin
13. Alphamethrin -continued 14. Amidoflumet
15. Amitraz
16. Anabasine
17. Avermectin B1
18. Azadirachtin
19. Azamethiphos
20. Azinphos-ethyl
21. Azinphos-methyl
22. Azocyclotin
23. *Bacillus* subtil, toxin
24. *Bacillus thuringiensis*
25. Benclothiaz
26. Bendiocarb
27. Benfuracarb
28. Bensultap
29. Benzoximate
30. Beta-cyfluthrin
31. Beta-cypermethrin
32. Bifenazate
33. Bifenthrin
34. Bioallethrin
35. Bioresmethrin
36. Bistrifluron
37. BPMC
38. Brofenprox
39. Bromophos A
40. Bromopropylate
41. Bufencarb
42. Buprofezin
43. Butocarboxim
44. Cadusafos
45. Carbaryl
46. Carbofuran
47. Carbophenothion
48. Carbosulfan
49. Cartap
50. Chloethocarb
51. Chlorantraniliprole
52. Chlorethoxyfos
53. Chlorfenapyr
54. Chlorfenvinphos
55. Chlorfluazuron
56. Chlormephos
57. Chlorpyrifos
58. Chlorpyrifos-methyl
59. Chromafenozide
60. Cis-Resmethrin
61. Clofentezin
62. Clothianidin
63. Coumaphos
64. Cyanophos
65. Cycloprothrin
66. Cyenopyrafen
67. Cyflumetofen
68. Cyfluthrin
69. Cyhalothrin
70. Cyhexatin
71. Cymiazole
72. Cypermethrin
73. Cyphenothrin
74. Cyromazine
75. Deltamethrin
76. Demeton M
77. Demeton S
78. Demeton-S-methyl
79. Diafenthiuron
80. Diazinon
81. Dichlofenthion
82. Dichlorvos
83. Dicofol
84. Dicrotophos
85. Dicyclanil
86. Diethion
87. Diflovidazin
88. Diflubenzuron
89. Dimefluthrin
90. Dimethoate
91. Dimethylvinphos
92. Dinobuton
93. Dinocap
94. Dinotefuran
95. Diofenolan
96. Dioxathion
97. Disulfoton
98. DNOC
99. Doramectin
100. DPX-HGW86
101. Edifenphos
102. Emamectin
103. Empenthrin
104. Endosulfan
105. Esfenvalerat
106. Ethiofencarb
107. Ethion
108. Ethiprole
109. Ethoprophos
110. Etofenprox
111. Etoxazole
112. Etrimphos
113. Fenamiphos
114. Fenazaquin
115. Fenbutatin oxide
116. Fenitrothion
117. Fenobucarb
118. Fenothiocarb
119. Fenoxycarb
120. Fenpropathrin
121. Fenpyroximate
122. Fenthion
123. Fenvalerate
124. Fipronil
125. Flonicamid
126. Fluacrypyrim
127. Fluazinam
128. Fluazuron
129. Flubendiamide
130. Flucycloxuron
131. Flucythrinate
132. Flufenerim
133. Flufenoxuron
134. Flufenprox
135. Flumethrin
136. Fonophos
137. Formothion
138. Fosthiazate
139. Fubfenprox
140. Furathiocarb
141. Gamma-cyhalothrin
142. Halfenprox
143. Halofenozide
144. HCH
145. Heptenophos
146. Hexaflumuron
147. Hexythiazox
148. Hydramethylnon
149. Hydroprene
150. Imidacloprid
151. Imiprothrin
152. Indoxacarb
153. insect-active fungi
154. insect-active nematodes
155. insect-active viruses
156. Iprobenfos
157. Lsofenphos
158. Isoprocarb
159. Isoxathion
160. Ivermectin
161. Karanjin
162. Kinoprene
163. Lamba-Cyhalothrin
164. Lepimectin
165. Lufenuron
166. Malathion
167. Mecarbam
168. Mesulfenphos
169. Metaflumizone
170. Metaldehyde
171. Methamidophos 172. Methidathion
173. Methiocarb
174. Methomyl
175. Methoprene
176. Methothrin
177. Methoxyfenozide
178. Metofluthrin
179. Metolcarb
180. Metoxadiazone
181. Mevinphos
182. Milbemectin
183. Milbemycin oxime
184. Monocrotophos
185. Moxidectin
186. Naled
187. Nicotine
188. Nitenpyram
189. Novaluron
190. Noviflumuron
191. Omethoate
192. Oxamyl
193. Oxydemethon M
194. Oxydeprofos
195. Parathion
196. Parathion-methyl
197. Permethrin
198. Phenothrin
199. Phenthoate
200. Phorate
201. Phosalone
202. Phosmet
203. Phosphamidon
204. Phoxim
205. Pirimicarb
206. Pirimiphos A
207. Pirimiphos M
208. Polynactins
209. Prallethrin
210. Profenofos
211. Profluthrin
212. Promecarb
213. Propafos
214. Propargite
215. Propoxur
216. Prothiofos
217. Prothoate
218. Protrifenbute
219. Pymetrozine
220. Pyrachlofos
221. Pyrafluprole
222. Pyresmethrin
223. Pyrethrin
224. Pyrethrum
225. Pyridaben
226. Pyridalyl
227. Pyridaphenthion
228. Pyrifluquinazon
229. Pyrimidifen
230. Pyriprole
231. Pyriproxyfen
232. Quinalphos
233. Resmethrin
234. Rotenone
235. RU 15525
236. Sabadilla
237. Salithion
238. Selamectin
239. Silafluofen
240. Spinetoram
241. Spinosad
242. Spirodiclofen
243. Spiromesifen
244. Spirotetramat
245. Sulcofuron sodium
246. Sulfluramid
247. Sulfotep
248. Sulfur
249. Sulprofos
250. Tau-fluvalinate
251. Tebufenozide
252. Tebufenpyrad
253. Tebupirimfos
254. Teflubenzuron
255. Tefluthrin
256. Temephos
257. Terbufos
258. Tetrachlorvinphos
259. Tetradifon
260. Tetramethrin
261. Thiacloprid
262. Thiamethoxam
263. Thiocyclam
264. Thiodicarb
265. Thiofanox
266. Thionazin
267. Thiosultap
268. Thuringiensin
269. Tolfenpyrad
270. Tralomethrin
271. Transfluthrin
272. Triarathene
273. Triazamate
274. Triazophos
275. Trichlorfon
276. Triflumuron
277. Trimethacarb
278. Vamidothion
279. Vaniliprole
280. XMC (3,5,-Xylylmethylcarbamate)
281. Xylylcarb
282. Zeta-cypermethrin
283. Zetamethrin
284. ZXI 8901
285. Demiditraz
286. Afoxolaner
287. Sarolaner
288. Fluralaner Non-limitative examples of suitable anthelmintics, a few representatives have anthelmintic activity in addition to the insecticidal and acaricidal activity include:

(A1) Abamectin      (A2) Albendazole       (A3) Cambendazole
(A4) Closantel      (A5) Diethylcarbamazine (A6) Doramectin
(A7) Emodepside     (A8) Eprinomectin      (A9) Febantel
(A10) Fendendazole  (A11) Flubendazole     (A12) Ivermectin
(A13) Levamisol     (A14) Mebendazole      (A15) Milbemectin
(A16) Milbemycin Oxime (A17) Morantel      (A18) Moxidectin
(A19) Nitroscanate  (A20) Omphalotin       (A21) Oxantel
(A22) Oxfendazole   (A23) Oxibendazole     (A24) Phenothiazine
(A25) Piperazine    (A26) PNU-97333        (A27) PNU-141962
(A28) Praziquantel  (A29) Pyrantel         (A30) Thiabendazole
(A31) Triclabendazole amino acetonitrile derivatives named in WO2005044784

Non-limiting examples of suitable repellents and detachers include: (R1) DEET (N,N-diethyl-m-toluamide); (R2) KBR 3023, picaridin, N-butyl-2-oxycarbonyl-(2-hydroxy)-piperidine; and (R3) Cymiazole, N,-2,3-dihydro-3-methyl-1,3-thiazol-2-ylidene-2,4-xylidene.

The above-specified combination partners are best known to specialists in this field. Most are described in various editions of the Pesticide Manual, The British Crop Protection Council, London, in various editions of the Compendium of Veterinary Products, North American Compendiums, Inc., in various editions of the Compendium of Pesticide Common Names, and in various editions of the Merck Veterinary Manual and The Merck Index, Merck & Co., Inc., Rahway, N.J., USA.

A pharmaceutical preparation comprising Compound A or a veterinary acceptable salt thereof for delivery to a human or other mammal, is preferably in unit dosage form, in which the preparation is subdivided into unit doses containing an appropriate quantity of the active component. The unit dosage form can be a packaged preparation containing discrete quantities of the preparation, such as packaged tablets, capsules, and powders in vials or ampoules. Also, the unit dosage form can be a capsule, tablet or lozenge itself, or it can be an appropriate number of any of these in packaged form.

The quantity of active component in a unit dose preparation can be varied or adjusted from about 0.1 mg to about 1000 mg, according to the particular application and the potency of the active component. The composition can, if desired, also contain other compatible therapeutic agents.

In therapeutic use for the treatment or prevention of a parasitic infection in a human or other mammal, the compounds utilized in the method of treatment are administered at an initial dosage of about 0.1 mg/kg to about 100 mg/kg per interval. Preferred intervals may be daily, weekly, semi-monthly, monthly, bi-monthly, quarterly, tri-annually, semi-annually, or annually. The dosages can be varied depending on the requirements of the patient, for example, the size of the human or mammal being treated, the severity of the condition being treated, the route of administration, and the potency of the compound(s) being used. Determination of the proper dosage and route of administration for a particular situation is within the skill of the practitioner. Generally, the treatment will be initiated with smaller dosages which are less than the optimum dose of the compound, which can be increased in small increments until the optimum effect under the particular circumstances of the infection is reached. For convenience, the total daily dosage can be divided and administered in portions during the day if desired.

Compound A, and compositions comprising a therapeutically effective amount of Compound A, an acceptable salt thereof, and a veterinary acceptable excipient, diluent, or carrier are useful as ectoparasiticides for the control and treatment of infections or infestations manifested by said ectoparasite in an animal. Compound A, or a veterinary acceptable salt thereof is an ectoparasiticide, in particular, as an acaricide and insecticide. Compound A or a veterinary acceptable salt thereof may be used in the fields of veterinary medicine, livestock husbandry, and the maintenance of public health: against acarids, insects, and copepods which are parasitic upon vertebrates, particularly warm-blooded vertebrates, including companion animals, livestock, and fowl and cold-blooded vertebrates like fish.

Non-limiting examples of ectoparasites include: ticks (e.g., *Ixodes* spp., (e.g., *I. ricinus*, *I. hexagonus*), *Rhipicephalus* spp. (e.g., *R. sanguineus*), *Boophilus* spp., *Amblyomma* spp. (e.g., *A. americanum*, *A. maculatum*, *A. triste*, *A. parvum*, *A. cajennense*, *A. ovale*, *A. oblongoguttatum*, *A. aureolatum*, *A. cajennense*), *Hyalomma* spp., *Haemaphysalis* spp., *Dermacentor* spp. (e.g., *D. variabilis*, *D. andersoni*, *D. marginatus*), *Ornithodorus* spp., and the like); mites (e.g., *Dermanyssus* spp., *Sarcoptes* spp. (e.g., *S. scabiei*), *Psoroptes* spp. (e.g., *P. bovis*), *Otodectes* spp., *Chorioptes* spp., *Demodex* spp., (e.g., *D. folliculorum*, *D. canis*, and *D. brevis*) and the like); chewing and sucking lice (e.g., *Damalinia* spp., *Linognathus* spp., *Cheyletiella* spp., *Haematopinus* spp., *Solenoptes* spp., *Trichodectes* spp., *Felicola* spp., and the like); fleas (e.g., *Siphonaptera* spp., *Ctenocephalides* spp., and the like); biting flies, midges, and mosquitos (e.g., *Tabanidae* spp., *Haematobia* spp., *Musca* spp., *Stomoxys* spp., *Dematobia* spp., *Cochliomyia* spp., *Simuliidae* spp., *Ceratopogonidae* spp., *Psychodidae* spp., *Aedes* spp., *Culex* spp., *Anopheles* spp., *Lucilia* spp., *Phlebotomus* spp., *Lutzomyia* spp., and the like); bed bugs (e.g., insects within the genus *Cimex* and family Cimicidae); and grubs (e.g., *Hypoderma bovis*, *H. lineatum*); and copepods (e.g., sea lice within the Order Siphonostomatoida, including genera *Lepeophtheirus* and *Caligus*).

Compound A or a veterinary acceptable salt thereof can also be used for the treatment of endoparasites, for example, helminths (e.g., trematodes, cestodes, and nematodes) including heartworm, roundworm, hookworm, whipworm, fluke, and tapeworm. The gastrointestinal roundworms include, for example, *Ostertagia ostertagi* (including inhibited larvae), *O. lyrata*, *Haemonchus placei*, *H. similis*, *H. contortus*, *Toxocara canis*, *T. leonina*, *T. cati*, *Trichostrongylus axei*, *T. colubriformis*, *T. longispicularis*, *Cooperia oncophora*, *C. pectinata*, *C. punctata*, *C. surnabada* (syn. *mcmasteri*), *C. spatula*, *Ascaris suum*, *Hyostrongylus rubidus*, *Bunostomum phlebotomum*, *Capillaria bovis*, *B. trigonocephalum*, *Strongyloides papillosus*, *S. ransomi*, *Oesophagostomum radiatum*, *O. dentatum*, *O. columbianum*, *O. quadrispinulatum*, *Trichuris* spp., and the like. Other parasites include: hookworms (e.g., *Ancylostoma caninum*, *A. tubaeforme*, *A. braziliense*, *Uncinaria stenocephala*); lungworms (e.g., *Dictyocaulus viviparus* and *Metastrongylus* spp); eyeworms (e.g., *Thelazia* spp.); parasitic stage grubs (e.g., *Hypoderma bovis*, *H. lineatum*, *Dermatobia hominis*); kidneyworms (e.g., *Stephanurus dentatus*); screw worm (e.g., *Cochliomyia hominivorax* (larvae); filarial nematodes of the super-family Filarioidea and the Onchocercidae Family. Non-limiting examples of filarial nematodes within the Onchocercidae Family include the genus *Brugia* spp. (i.e., *B. malayi*, *B. pahangi*, *B. timori*, and the like), *Wuchereria* spp. (i.e., *W. bancrofti*, and the like), *Dirofilaria* spp. (*D. immitis*, *D. repens*, *D. ursi*, *D. tenuis*, *D. spectans*, *D. lutrae*, and the like), *Dipetalonema* spp. (i.e., *D reconditum*, *D. repens*, and the like), *Onchocerca* spp. (i.e., *O. gibsoni*, *O. gutturosa*, *O. volvulus*, and the like), *Elaeophora* spp. (*E. bohmi*, *E. elaphi*, *E. poeli*, *E. sagitta*, *E. schneideri*, and the like), *Mansonella* spp. (i.e., *M. ozzardi*, *M. perstans*, and the like), and *Loa* spp. (i.e., *L. loa*).

Preferably, Compound A or a veterinary acceptable salt thereof may be used to treat parasitic infection or infestation, preferably wherein the parasite is a flea or tick. In particularly preferred embodiments, the parasite is *C. fells*, *R. sanguineis*, *A. americanum*, *I. scapularis*, *A. maculate*, *D. variabilis*, or *I. ricinus*.

In another aspect of the invention, Compound A or a veterinary acceptable salt thereof is useful for treating endoparasiticidal infection from helminths/filarial nematodes within the genus *Dirofilaria* (i.e., *D. immitis*, *D. repens*, *D. ursi*, *D. tenuis*, and the like).

Compound A, and veterinary or pharmaceutical acceptable salts thereof, and compositions comprising compounds of the present invention in conjunction with at least one other veterinary agent are of particular value in the control of ectoparasites, endoparasites, and insects which are injurious to, or spread or act as vectors of diseases in companion animals, livestock, birds, and fish.

Compound A or a veterinary acceptable salt thereof, or a suitable combination of Compound A or a veterinary acceptable salt thereof and optionally, with at least one additional veterinary agent may be administered directly to the animal and/or indirectly by applying it to the local environment in which the animal dwells (such as bedding, enclosures, and the like). Direct administration includes contacting the skin, fur, or feathers of a subject animal with the compound(s), or by feeding or injecting the compounds into the animal.

Compound A or a veterinary acceptable salt thereof, and combinations with at least one additional veterinary agent, as described herein, are believed to be of value for the treatment and control of the various lifecycle stages of insects and parasites including egg, nymph, larvae, juvenile and adult stages.

The present invention also relates to a method of administering Compound A or a veterinary acceptable salt thereof alone or in combination with at least one additional veterinary agent, and optionally a veterinary acceptable excipient, diluent, or carrier, to animals in good health comprising the application to said animal to reduce or eliminate the potential for human parasitic infection or infestation from parasites carried by the animal and to improve the environment in which the animals inhabit.

EXAMPLES

Experimental Procedures:

Liquid chromatography-mass spectrometry (LCMS) experiments to determine retention times and associated mass ions were performed using one or more of the following Methods A, B, and C:

Method A: Waters BEH (ethylene bridged hybrid) $C_{18}$ column, 3.0×30 mm, 1.7 μm, was used at a temperature of 50° C. and at a flow rate of 1.5 mL/min, 2 μL injection, mobile phase: (A) water with 0.1% formic acid and 1% acetonitrile, mobile phase; (B) MeOH with 0.1% formic acid; retention time given in minutes.

Method A details: (I) ran on a Binary Pump G1312B, Agilent Technologies, with UV/Vis diode array detector G1315C and Agilent 6130 mass spectrometer in positive and negative ion electrospray mode with UV PDA detection with a gradient of 15-95% (B) in a 2.2 min linear gradient (II) hold for 0.8 min at 95% (B) (III) decrease from 95-15% (B) in a 0.1 min linear gradient (IV) hold for 0.29 min at 15% (B);

Method B: An Agilent Zorbax Bonus RP column, 2.1×50 mm, 3.5 μm, was used at a temperature of 50° C. and at a flow rate of 0.8 mL/min, 2 μL injection, mobile phase: (A) water with 0.1% formic acid and 1% acetonitrile, mobile phase (B) MeOH with 0.1% formic acid; retention time given in minutes.

Method B details: (I) ran on a Binary Pump G1312B, Agilent Technologies, with UV/Vis diode array detector G1315C and Agilent 6130 mass spectrometer in positive and negative ion electrospray mode with UV-detection at 220 and 254 nm with a gradient of 5-95% (B) in a 2.5 min linear gradient (II) hold for 0.5 min at 95% (B) (III) decrease from 95-5% (B) in a 0.1 min linear gradient (IV) hold for 0.29 min at 5% (B).

Method C: An API 150EX mass spectrometer, Applied Biosystems, linked to a Shimadzu LC-10AT liquid chromatography system, with a diode array detector was used. The spectrometer had an electrospray source operating in positive and negative ion mode. The liquid chromatography was carried out using an Agilent ZORBAX XDB 50×2.1 mm $C_{18}$ column and a 0.5 mL/minute flow rate. Solvent A: 95% water, 5% acetonitrile containing 0.01% formic acid; Solvent B: acetonitrile. The gradient was shown 0-0.5 min: 2% solvent (B); 0.5-2.5 min: 2% solvent B to 95% solvent (B); 2.5-4.0 min: 95% solvent (B); 4.0-4.2 min: 95% solvent (B) to 2% solvent B; 4.2-6.0 min: 2% solvent (B).

Example 1A 1-(3,3,3-Trifluoropropanoyl)azetidin-3-one

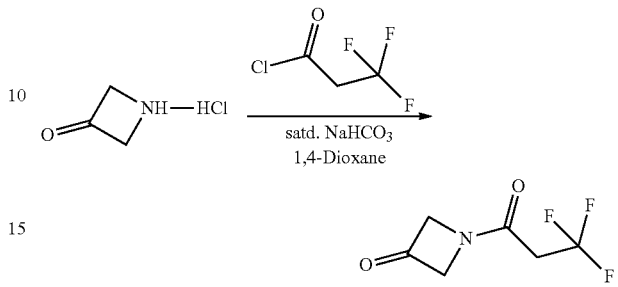

3-Azetidinone hydrochloride (10 g, 93 mmol) was taken up in 1,4-dioxane (150 mL). An aqueous solution of saturated bicarbonate (100 mL) was added. The heterogeneous mixture was stirred for 20 min and a solution of 3,3,3-trifluoropropanoyl chloride (20.43 g, 139.5 mmol) in 1,4-dioxane (50 mL) was added dropwise. The solution turned homogeneous and the resulting solution was allowed to stir for 16h. The reaction was treated with 20 g of solid $NaHCO_3$ and stirred for 20 min. The solid was filtered and concentrated. The residue was dissolved in 250 mL of DCM and washed with (2×50 mL) of 1N HCl, brine and dried over anhydrous $MgSO_4$, filtered and concentrated to give an off-white liquid which on standing under vacuum gave 6 g (36%) solid 1-(3,3,3-trifluoropropanoyl)azetidin-3-one. m/e (M+H) 182. 1H NMR (400 MHz, DICHLOROMETHANE-d2) δ ppm 3.14-3.25 (m, 2 H) 4.81 (br. s., 2 H) 4.93 (br. s., 2 H).

1-(6-Bromospiro[1H-isobenzofuran-3,3'-azetidine]-1'-yl)-3,3,3-trifluoro-propan-1-one (Intermediate Compound 1), which also may be referred to as 1-(5'-bromo-3'H-spiro [azetidine-3,1'-isobenzofurn]-1-yl)-3,3,3-trifluoropropan-1-one, depending upon the naming convention used.)

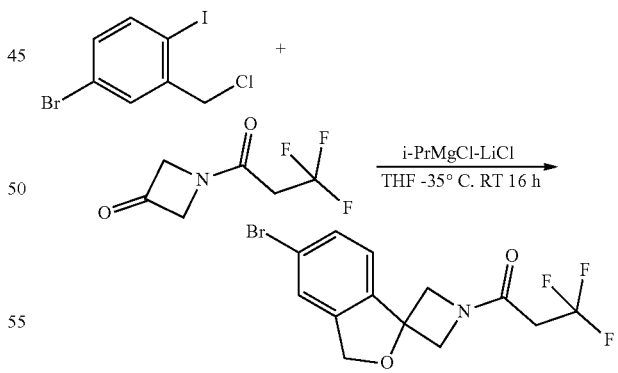

4-Bromo-2-(chloromethyl)-1-iodo-benzene (3.3 g, 10.0 mmol) was dissolved in tetrahydrofuran (THF) (25 mL) and cooled to −35° C. under $N_2$. i-PrMgCl—LiCl (6.1 mL, 8.0 mmol, 1.3 M in THF) was added dropwise while keeping the cold bath temperature between −33° C. and −36° C. The reaction was stirred within this temperature range for 45 min. A solution of 1-(3,3,3-trifluoropropanoyl)azetidin-3-one (1.8 g, 10 mmol) in THF (20 mL) was cooled to −35° C. in another flask under $N_2$. The Grignard solution was

1-(5'-bromo-3'H-spiro[azetidine-3,1'-isobenzofuran]-1-yl)-3,3,3-trifluoropropan-1-one (Intermediate Compound 1)

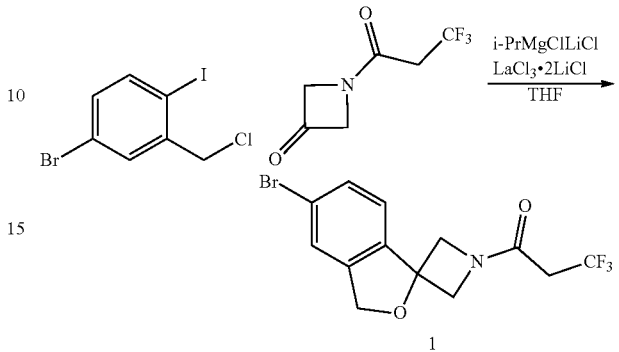

Note, this reaction was found to be sensitive to water. Depending on water content of LaCl$_3$.2LiCl solution used, azeotropic distillation may need to be modified to remove appropriate amount of water contaminant.

A solution of LaCl$_3$.2LiCl (121 mL, 0.6 molar in THF 72.5 mmol) was diluted with anhydrous THF (2×100 mL) and azeotroped at room temperature and 1 atm (removed 2×100 mL of THF). 1-(3,3,3-Trifluoropropanoyl)azetidin-3-one (10.5 g, 58.0 mmol) was added to the anhydrous LaCl$_3$.2LiCl solution and stirred for 2.5 hours while the aryl Grignard solution was made.

To a cooled (−35° C.) solution of 2-iodo-5-bromobenzyl chloride (24.0 g, 72.5 mmol) in anhydrous THF (200 mL) was added a solution of i-PrMgCl.LiCl (58.0 mL, 1.3 molar, 75.4 mmol) in THF while maintaining an internal temperature of <−30° C. The aryl Grignard solution was then maintained between −35 and −40° C. for 90 min.

The LaCl$_3$.2LiCl/azetidinone complex was cooled to −10° C. (*note, further cooling of La complex solution resulted in the solution turning into a gel). The cooled (−35° C.) aryl Grignard solution was cannulated into the LaCl3.2LiCl/azetidinone solution at a rate that kept the internal temperature of the LaCl3.2LiCl/azetidinone solution between −10 and −20° C. The reaction was allowed to warm to room temperature over 2 hours and further stirred at room temperature for 19 hours. The reaction was quenched with aq. citric acid (150 mL, 1 molar) and extracted with EtOAc (1×300 mL and 1×150 mL). The combined organic fractions were washed 1×150 mL saturated aq. NaHCO$_3$, 1×150 mL saturated aq NaCl, dried with Na$_2$SO$_4$, filtered and concentrated in vacuo. The resultant residue was chromatographed over silica gel (Isco 220 g cartridge, gradient 0 to 45% EtOAc in heptanes over 45 min) to give 14.4 g of 1-(5'-bromo-3'H-spiro[azetidine-3,1'-isobenzofuran]-1-yl)-3,3,3-trifluoropropan-1-one (71%). Yields for smaller scale reactions have ranged between 62-71% for this experiment.

$^1$H NMR (400 MHz, CHLOROFORM-d) δ=7.54 (td, J=0.9, 8.1 Hz, 1H), 7.40 (d, J=0.9 Hz, 1H), 7.30 (d, J=8.1 Hz, 1H), 5.13 (s, 2H), 4.57 (dd, J=1.2, 9.2 Hz, 1H), 4.45-4.37 (m, 2H), 4.33-4.28 (m, 1H), 3.07 (dq, J=2.2, 10.3 Hz, 2H).

An alternate method for making Intermediate Compound 1 may be used.

added via cannula to this solution slowly and the reaction was stirred and warmed to room temperature over 2 h, then stirred at this temperature for 16 h. The reaction was slowly quenched with aqueous citric acid (1 M, 30 mL), diluted with methyl-t-butyl ether (MTBE) (30 mL), mixed and the layers separated. The aqueous phase was further extracted with MTBE (2×30 mL) and the combined organic layers was washed with saturated NaHCO$_3$ (2×30 mL), brine (1×30 mL), dried (Na$_2$SO$_4$), filtered and evaporated. The residue was loaded onto Celite and purified by chromatography on silica gel (40 g cartridge) with 0-60% Ethyl acetate/Heptanes to give a white solid. Yield 0.504 g (18%). LC-MS (M+H) 351

$^1$H NMR (400 MHz, CHLOROFORM-d) δ ppm 2.97-3.11 (m, 2 H) 4.28 (dd, J=10.98, 1.27 Hz, 1 H) 4.33-4.45 (m, 2 H) 4.55 (dd, J=9.10, 1.15 Hz, 1 H) 7.16-7.32 (m, 2 H) 7.38 (d, J=0.98 Hz, 1 H) 7.52 (dt, J=8.10, 0.83 Hz, 1 H).

An alternate method for making Intermediate Compound 1 may be used.

Example 1B

1-(3,3,3-Trifluoropropanoyl)azetidin-3-one

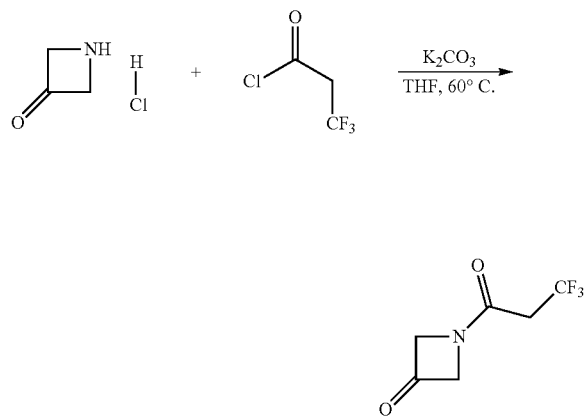

To a cooled (0° C.) suspension of 3-azetidinone hydrochloride (15.0 g, 139 mmol) and K$_2$CO$_3$ (48.2 g, 349 mmol) in THF (0.23 L) was added 3,3,3-trifluoropropionyl chloride (24.5 g, 167 mmol). Reaction was heated to 60° C. for 2 hours, cooled to room temperature and filtered. The solids were washed 1×0.2 L EtOAc and the combined organic solutions were washed 1×0.2 L saturated aq. NaHCO$_3$. The aqueous layer was extracted 4×100 mL EtOAc and the combined organic fractions were dried with Na$_2$SO$_4$. The suspension was filtered and concentrated in vacuo to give an oil that solidified on standing. The solid was dissolved in minimal amount of EtOAc at room temperature and diluted with 4 volumes of heptanes dropwise while stirring overnight. The resultant solids were filtered and placed under high vacuum for 4 hours to give 16.5 g of 1-(3,3,3-trifluoropropanoyl)azetidin-3-one (65%).

$^1$H NMR (400 MHz, CHLOROFORM-d) δ=5.00-4.81 (m, 4H), 3.25-3.11 (m, 2H).

Example 1C

Phenyl 3-oxoazetidine-1-carboxylate

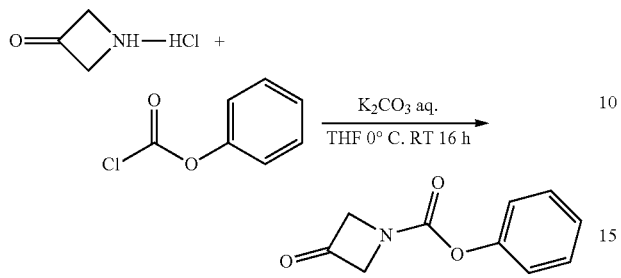

A suspension of azetidinone hydrochloride (2.0 g, 18.6 mmol) in THF (15 mL) under $N_2$ was treated with phenyl chloroformate (3.6 mL, 27.9 mmol). To the resulting mixture was added dropwise a solution of $K_2CO_3$ (7.7 g, 55.8 mmol) in water (20 mL) at 0° C. After the addition, the reaction mixture was allowed to warm to room temperature and stirred overnight. The reaction was extracted with ethyl acetate (3×50 mL), washed with brine, dried ($Na_2SO_4$), filtered and evaporated. The residue was loaded onto Celite and purified by chromatography on silica gel (80 g cartridge) with 0-60% Ethyl acetate/Heptanes to give a white solid. Yield 2.74 g (77.2%).

$^1$H NMR (400 MHz, CDCl3) δ ppm 7.37-7.43 (m, 2H), 7.22-7.27 (m, 1H), 7.14-7.19 (m, 2H), 4.94 (s, 4H); LCMS-ELSD m/z=210.2 (M+H$_3$O+).

Phenyl 6-bromospiro[1H-isobenzofuran-3,3'-azetidine]-1'-carboxylate

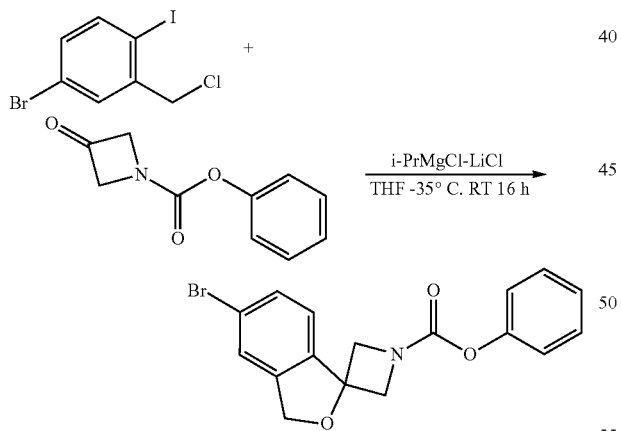

4-Bromo-2-(chloromethyl)-1-iodo-benzene (3.90 g, 11.77 mmol) was dissolved in THF (30 mL) and cooled to −35° C. under $N_2$. i-PrMgCl—LiCl (9.37 mL, 12.23 mmol, 1.3 M in THF) was added dropwise while keeping the cold bath temperature between −33° C. and −36° C. The reaction was stirred within this temperature range for 1.5 h. A solution of phenyl 3-oxoazetidine-1-carboxylate (2.70 g, 14.12 mmol) in THF (10 mL) was added dropwise while maintaining the cold bath temperature range. The reaction was slowly warmed to room temperature over 2 h, then stirred at this temperature for 16 h. The reaction was slowly quenched with aqueous citric acid (1 M, 30 mL), diluted with MTBE (30 mL), mixed and the layers separated. The aqueous phase was further extracted with MTBE (2×30 mL) and the combined organic layers was washed with saturated $NaHCO_3$ (2×30 mL), brine (1×30 mL), dried ($Na_2SO_4$), filtered and evaporated. The residue was loaded onto Celite and purified by chromatography on silica gel (40 g cartridge) with 0-60% Ethyl acetate/Heptanes to give a white solid. Yield 3.61 g (85.1%).

$^1$H NMR (400 MHz, CDCl3) δ ppm 7.56 (dt, J=8.1, 0.8 Hz, 1H), 7.35-7.45 (m, 4H), 7.19-7.25 (m, 1H), 7.15-7.19 (m, 2H), 5.14 (s, 2H), 4.53 (br. s., 2H), 4.35 (br. s., 2H); LCMS-ELSD m/z=360.0 (M+H).

6-Bromospiro[1H-isobenzofuran-3,3'-azetidine]

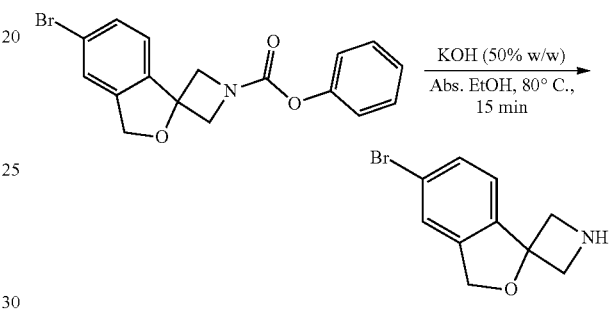

Phenyl 6-bromospiro[1H-isobenzofuran-3,3'-azetidine]-1'-carboxylate (1.01 g, 2.80 mmol) was placed in a 100 mL round bottom flask, then followed by absolute EtOH (40 mL). To the suspension was added KOH (50% w/w, aq; 13.5 mL), the flask placed into an 80° C. preheated oil bath and stirred for 15 minutes under $N_2$. Ethanol was removed by evaporation, the residue carefully acidified with 2 N HCl (80 mL) to pH 3-4 and extracted with $Et_2O$ (50 mL) to get rid of phenol byproduct. The aqueous layer was basified with KOH (50% aq w/w) to pH 13-14, then extracted with ethyl acetate (3×100 mL) and concentrated to a white solid. Crude Yield 710 mg (105%).

$^1$H NMR (400 MHz, CD3OD) δ ppm 7.64 (d, J=8.1 Hz, 1H), 7.53 (d, J=8.1 Hz, 1H), 7.42 (s, 1H), 5.03 (s, 2H), 4.05 (d, J=9.9 Hz, 2H), 3.78 (d, J=9.7 Hz, 2H); LCMS-ELSD m/z=240.0 (M+H).

1-(6-Bromospiro[1H-isobenzofuran-3,3'-azetidine]-1'-yl)-3,3,3-trifluoro-propan-1-one

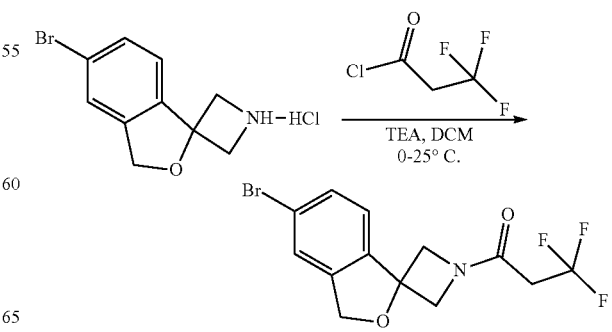

HCl salt of 6-bromospiro[1H-isobenzofuran-3,3'-azetidine] (3.24 g, 11.7 mmol) was taken up in dichloromethane (DCM) (50 mL) and cooled to 0° C. Triethylamine (TEA) (8.1 mL, 58.5 mmol) was added to this and stirred for 5 min. 3,3,3-trifluoropropanoyl chloride (2.05 g, 14.04 mmol) was added to this slowly and the resulting mixture was stirred for 6h at 0-25° C. The reaction mixture was diluted with DCM (50 mL) and washed with water (20 mL), saturated NaHCO₃ solution (20 mL) and brine (20 mL). The organic layer was dried over anhydrous MgSO₄ and concentrated. The crude was loaded on celite and purified on silica gel using heptane/ethyl acetate as eluent to give desired product. (3.1 g, 75%).

¹H NMR (400 MHz, CHLOROFORM-d) δ ppm 2.97-3.11 (m, 2 H) 4.28 (dd, J=10.98, 1.27 Hz, 1 H) 4.33-4.45 (m, 2 H) 4.55 (dd, J=9.10, 1.15 Hz, 1 H) 7.16-7.32 (m, 2 H) 7.38 (d, J=0.98 Hz, 1 H) 7.52 (dt, J=8.10, 0.83 Hz, 1 H).

An alternate method for making Intermediate Compound 1 may be used.

Example 1D

Phenyl 3-oxoazetidine-1-carboxylate

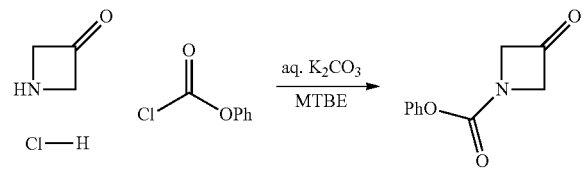

To a cooled (0° C.) mixture of 3-azetidinone hydrochloride (1.50 kg, 14.0 mol) in MTBE (19.0 L) was added phenyl chloroformate (2.63 L, 20.9 mol). Reaction was then cooled to (−10° C.) before a solution of aq. K₂CO₃ (18.8 L, 2.23 molar, 41.9 mol) was added while the internal temperature was maintained below 10° C. Water and ice from ice bath were siphoned off and reaction allowed to stir at room temperature for 15 hours. The mixture was filtered and mother liquor layers were separated. The aqueous layer was extracted 1×4 L EtOAc and the combined organic fractions were washed 1×4 L 20% brine. The organic solution was dried with MgSO₄ and filtered. The solids from the filtration were suspended in EtOAc (16 L) and washed 2×4 L water and 1×4 L 20% brine. The organic solution was dried with MgSO₄ and filtered. Both organic solutions were combined and concentrated in vacuo to give an oil that solidified on standing (3.32 kg). The solid was dissolved in EtOAc (2.5 L) at 50° C. and heptane (5.0 L) was slowly added with stirring while continuing to heat at 50° C. The solution was then allowed to cool to 10° C. over 2 hours.

The resultant suspension was filtered and rinsed with heptanes/EtOAc (2:1, 2×2 L) and heptanes (1×2 L). Solids were then dried over 16 hours to give 1.73 kg of phenyl 3-oxoazetidine-1-carboxylate (65%).

¹H NMR (400 MHz, CHLOROFORM-d) δ=7.46-7.38 (m, 2H), 7.30-7.24 (m, 1H), 7.22-7.16 (m, 2H), 4.96 (s, 4H).

Phenyl 5'-bromo-3'H-spiro[azetidine-3,1'-isobenzofuran]-1-carboxylate

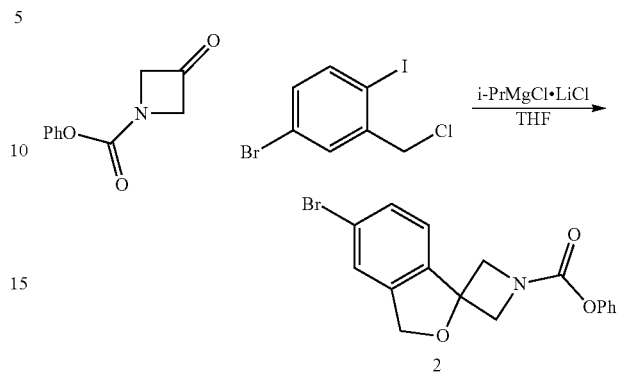

To a cooled (−30° C.) solution of 2-iodo-5-bromobenzylchloride (2.09 kg, 6.32 mol) in THF (8.0 L) was added a solution of i-PrMgCl.LiCl (5.35 L, 6.95 mol, 1.3 molar) while maintaining the internal temperature <−25° C. Reaction was allowed to stir at −35° C. for 1.5 h before a solution of phenyl 3-oxoazetidine-1-carboxylate (1.45 kg, 7.58 mol) was added while maintaining the internal temperature <−25° C. Reaction was then allowed to gradually warm over 15 hours. Reaction was warmed to 35° C. for 4 hours before it was quenched with aq. citric acid (6.34 L, 2.00 molar). Biphasic layers were diluted with MTBE (15 L) and mixed before removing the organic fraction. The aqueous layer was extracted 2×1 L MTBE and the combined organic fractions were washed 3×5 L saturated aq. NaHCO₃. The last aq. wash was confirmed to have a pH >7. Organic solution was washed 1×4 L 20% aq NaCl, dried with MgSO₄, filtered and concentrated in vacuo to give 2.70 kg of a solid. The solid was suspended in absolute EtOH (8.3 L) and placed in a 50° C. water bath for 30 min. before the water bath was removed for 30 min. Mixing was used during the entire heat/cool cycle and the heat/cool cycle was repeated four additional times. After the last heat cycle, the power was turned off to the water bath and the crystallization was allowed to slowly cool to room temperature in the water bath over 15 hours while mixing. Suspension was filtered and the solids were rinsed with cold (4° C.) absolute EtOH (5 L). Solids were transferred into trays and dried under high vac. for 15 hours to give 1.76 kg of phenyl 5'-bromo-3'H-spiro[azetidine-3,1'-isobenzofuran]-1-carboxylate (77%).

¹H NMR (400 MHz, CHLOROFORM-d) δ=7.55 (dd, J=0.8, 8.1 Hz, 1H), 7.45-7.34 (m, 4H), 7.26-7.14 (m, 3H), 5.14 (s, 2H), 4.53 (br. s., 2H), 4.35 (br. s., 2H).

5'-bromo-3'H-spiro[azetidine-3,1'-isobenzofuran] hydrochloride

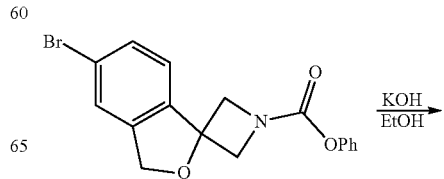

-continued

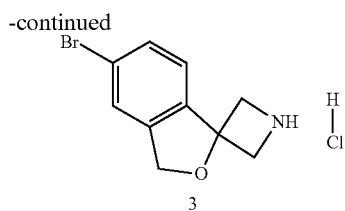

To a warm (40° C.) mixture of phenyl 5'-bromo-3'H-spiro [azetidine-3,1'-isobenzofuran]-1-carboxylate (631 g, 1.75 mol) in EtOH (4.38 L), was added 50% aq. KOH (1.46 L). Reaction was heated to 60° C. for 1.75 hours. TLC and LCMS confirmed no starting material or ethyl carbonate was present before reaction was cooled to room temperature. Reaction pH was adjusted to 10-11 with 6 molar HCl (2.8 L) before EtOH was removed by distillation under reduced pressure. After all the EtOH was removed, 6 molar HCl was slowly added to control gas evolution, until pH was 2-3. Reaction was stirred ½ hour before the pH was readjusted to 7 with 50% aq. KOH and allowed to cool to room temperature over 15 hours. Reaction pH was adjusted to 12-13 with 50% aq. KOH before it was diluted with EtOAc (2.5 L) and water (2 L). Vigorous stirring for % hour was used to get most of the precipitates into solution. Phase separation was carried out over 15 min. and organic phase isolated. Aq. suspension was extracted 4×2.5 L EtOAc and combined organic fractions were washed 1×1.2 L saturated aq NaCl, dried with $Na_2SO_4$, filtered and concentrated to give 577 g of a brown oil. Oil was dissolved in EtOH (1.1 L) and a solution of HCl in dioxane (0.88 L, 4 molar) was added and reaction mixed for % hour. The reaction was concentrated in vacuo to give a solid that was suspended in dioxane (0.88 L). The suspension was heated to 50° C. with mixing for % hour before allowing the suspension to cool at room temperature for % hour. Heat/cool cycle was repeated 4 additional times and after last heating, the power was turned off the water bath and the suspension was allowed to slowly cool to room temperature over 15 hours. The mixing was stopped and the resultant suspension was filtered and rinsed with dioxane (0.3 L). The solids were allowed to air dry on the funnel under vacuum to give 401 g of 5'-bromo-3'H-spiro[azetidine-3,1'-isobenzofuran]hydrochloride (83%).

Note that yields for smaller scale reactions have ranged between 80-93% for this experiment.

$^1$H NMR (400 MHz, METHANOL-$d_4$) δ=7.72-7.67 (m, 1H), 7.64-7.60 (m, 1H), 7.52 (d, J=0.7 Hz, 1H), 5.13 (s, 2H), 4.50-4.40 (m, 4H).

1-(5'-bromo-3'H-spiro[azetidine-3,1'-isobenzofuran]-1-yl)-3,3,3-trifluoropropan-1-one (Intermediate Compound 1)

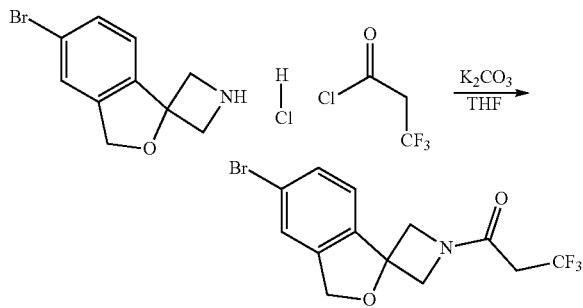

To a mixture of 3 (458 g, 1.66 mol) and $K_2CO_3$ (687 g, 4.97 mol) in THF (4.60 L) was added 3,3,3-trifluorpropionyl chloride (303 g, 2.07 mol). Reaction was heated to 60° C. for 3 hours before it was cooled to room temperature and quenched with water (2.30 L). Heptane (2.30 L) was added and stirred for 1/2 hour. The organic layer was removed and the aq. layer was extracted 1×1 L EtOAc. The combined organic fractions were dried with $Na_2SO_4$, filtered and concentrated in vacuo to give 580 g of 1-(5'-bromo-3'H-spiro[azetidine-3,1'-isobenzofuran]-1-yl)-3,3,3-trifluoropropan-1-one (quantitative).

Note: yields for smaller scale reactions have ranged between 78% —quantitative for this experiment.

$^1$H NMR (400 MHz, CHLOROFORM-d) δ=7.54 (td, J=0.9, 8.1 Hz, 1H), 7.40 (d, J=0.9 Hz, 1H), 7.30 (d, J=8.1 Hz, 1H), 5.13 (s, 2H), 4.57 (dd, J=1.2, 9.2 Hz, 1H), 4.45-4.37 (m, 2H), 4.33-4.28 (m, 1H), 3.07 (dq, J=2.2, 10.3 Hz, 2H).

Example 1E

An alternate method for making Intermediate Compound 1 may be used.

6'-Bromo-2,2-dimethyl-spiro[1,3-dioxane-5,3'-1H-isobenzofuran]

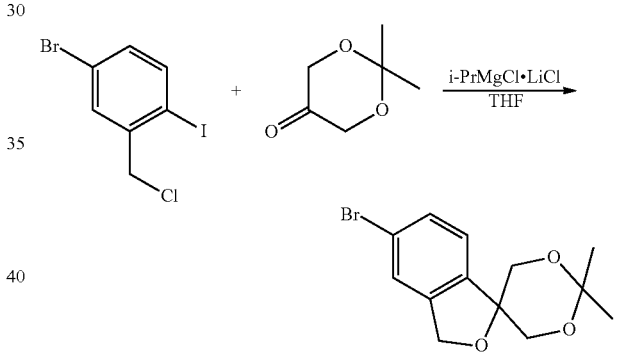

4-Bromo-2-(chloromethyl)-1-iodo-benzene (50.0 g, 150.9 mmol) was dissolved in dry THF (400 mL) and cooled to −35° C. (internal temperature). Iso-PrMgCl·LiCl (128.0 mL, 166.0 mmol, 1.3 M solution in THF) was added at −35° C. (internal temp) and stirred at −35° C. for 90 min. 2,2-Dimethyl-1,3-dioxan-5-one (23.6 g, 181.1 mmol) in dry THF (20 mL, 15+5 mL rinse) was added while the internal temperature was maintained at −35° C. and the reaction mixture was slowly warmed to room temperature and stirred overnight under nitrogen. The reaction was quenched with 1.0 M aqueous citric acid (100 mL) and extracted with MTBE (2×100 mL), washed with sat-NaHCO$_3$ (2×150 mL), brine (1×150 mL), and dried over anhydrous sodium sulfate. After solvents removal, the crude product was dissolved in about one volume of ethyl acetate (~50 mL) and heated until a homogeneous solution was obtained. It was cooled to room temperature and then stored in the refrigerator overnight. The supernatant was removed via syringe and saved. The solid was triturated with cold MTBE (~50 mL) and the organic layer was removed via syringe and saved. The solid was dried under vacuum to yield 25 g of pure product. The supernatants were combined, concentrated, and purified via silica gel chromatography (330 g RediSep cartridge, 0 to 20% ethyl acetate in heptanes) to yield 7.5 g of extra amount of product. Total amount: 32.5 g (72%).

¹H NMR (400 MHz, CHLOROFORM-d) δ ppm 1.56 (s, 3 H,) 1.57 (s, 3 H,) 3.86-3.99 (m, 4 H), 5.12 (s, 2 H), 7.34 (d, J=8.10 Hz, 1 H), 7.36-7.39 (m, 1 H), 7.42-7.46 (m, 1 H).

[5-Bromo-1-(hydroxymethyl)-3H-isobenzofuran-1-yl]methanol

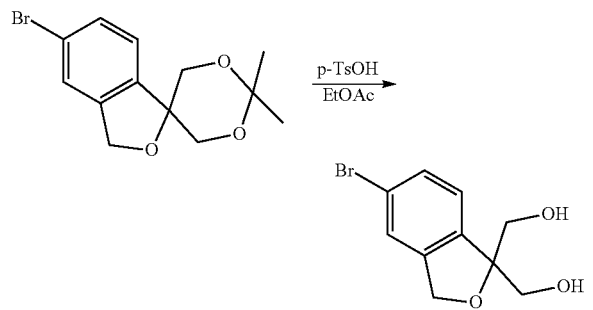

To a cold solution (0° C., ice-bath) of 6'-bromo-2,2-dimethyl-spiro[1,3-dioxane-5,3'-1H-isobenzofuran] (4.75 g, 15.9 mmol) in EtOAc (80.0 mL) was added p-toluenesulfonic acid monohydrate (18.4 g, 96.8 mmol) and the resulting mixture was stirred at this temperature for 60 min. It was quenched by slowly pouring into a beaker of sat-NaHCO₃ (200 mL) and extracted with ethyl acetate (2×150 mL). The combined organic extracts were washed with saturated sodium chloride solution (1×100 mL) and then concentrated to yield 4.27 g of product (100%); LC/MS, 241.0 [M–H₂O].

[5-Bromo-1-[(4-nitrophenyl)sulfonyloxymethyl]-3H-isobenzofuran-1-yl]methyl 4-nitrobenzenesulfonate

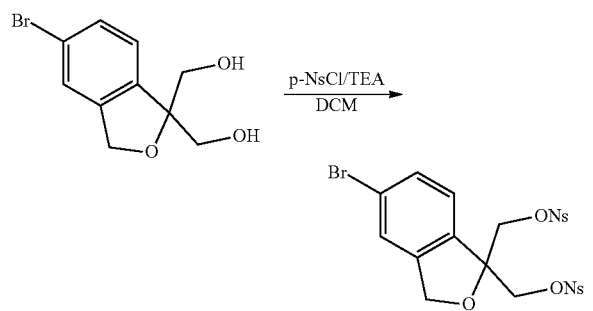

[5-Bromo-1-(hydroxymethyl)-3H-isobenzofuran-1-yl] methanol (2.25 g, 8.68 mmol) was dissolved dry DCM (60 mL) containing 4-DMAP (100 mg) and cooled to 0° C. TEA (2.7 mL, 19.1 mmol) and 4-nitrobenzenesulfonyl chloride (4.0 g, 18.2 mmol) were added and the reaction mixture was stirred at 0° C. to RT for 20 h. The precipitate was filtered, washed with DCM (2×10 mL), water (2×10 mL), and dried under vacuum to yield 3.93 g of product. The DCM wash was saved and the water wash was extracted with DCM (2×10 mL) then combined with the DCM wash and concentrated. The residue was purified using flash silica gel column chromatography, eluting with 0 to 30% ethyl acetate in heptanes to yield 0.25 g product. Total product amount=4.18 g (76.5%).

¹H NMR (400 MHz, DMSO-d₆) δ ppm 4.43 (q, J=10.71 Hz, 4 H), 4.79 (s, 2 H), 7.09 (d, J=8.10 Hz, 1 H), 7.32 (dd, J=8.10, 1.66 Hz, 1 H), 7.45 (d, J=1.17 Hz, 1 H,) 8.00 (d, J=8.88 Hz, 4 H), 8.39 (d, J=8.88 Hz, 4 H).

6-Bromo-1'-(2-nitrophenyl)sulfonyl-spiro[1H-isobenzofuran-3,3'-azetidine]

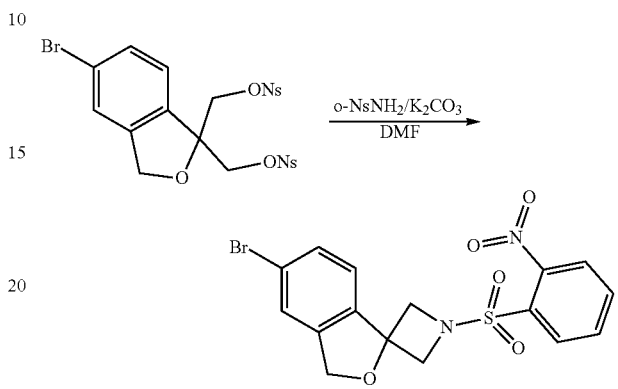

[5-bromo-1-[(4-nitrophenyl)sulfonyloxymethyl]-3H-isobenzofuran-1-yl]methyl 4-nitrobenzenesulfonate (4.0 g, 6.36 mmol) and 2-nitrobenzenesulfonamide (1.35 g, 6.67 mmol) were dissolved in DMF (70.0 mL). Potassium carbonate (1.76 g, 12.71 mmol) was added and the mixture was stirred at 100° C. for 24 h under nitrogen. It was cooled down to room temperature, diluted with water (150 mL), and extracted with ethyl acetate (3×100 mL). The combined organic extracts were washed with brine (1×150 mL), dried over anhydrous sodium sulfate, and concentrated. The residue was purified using silica gel column chromatography (0 to 40% ethyl acetate in heptane) to yield 1.71 g of the azetidine product (63%).

¹H NMR (400 MHz, DMSO-d₆) δ ppm 4.17-4.29 (m, 4 H), 5.00 (s, 2 H), 7.28 (d, J=8.10 Hz, 1 H), 7.53-7.61 (m, 2 H), 7.93-7.99 (m, 1 H), 8.02 (td, J=7.69, 1.51 Hz, 1 H), 8.08-8.12 (m, 1 H), 8.15 (dd, J=7.76, 1.51 Hz, 1 H); LC/MS, 426.8 [M+H]⁺.

1-(6-Bromospiro[1H-isobenzofuran-3,3'-azetidine]-1'-yl)-3,3,3-trifluoro-propan-1-one (Intermediate Compound 1)

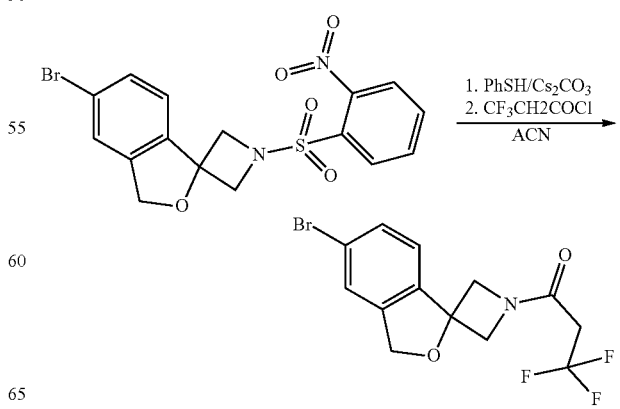

Cesium carbonate (2.56 g, 3.93 mmol) and thiophenol (0.44 mL, 4.32 mmol) were successively added to a solution of 6-bromo-1'-(2-nitrophenyl)sulfonyl-spiro[1H-isobenzofuran-3,3'-azetidine] (1.67 g, 3.93 mmol) in acetonitrile (30 mL). The mixture was stirred at room temperature for 1 h. After this time the starting material was consumed as judged by TLC. Another 960 mg (0.75 eq) of cesium carbonate was added, followed by the addition of 0.61 g (4.12 mmol) of 3,3,3-trifluoropropionyl chloride in ACN (1.5 mL). The resulting mixture was heated to 60° C. and stirred at this temperature for 30 min. It was cooled down to RT and diluted with water (50 mL) and extracted with ethyl acetate (2×50 mL). The organic extract was washed with brine (1×50 mL) and concentrated under reduced pressure. The residue was purified using silica gel chromatography (0 to 50% ethyl acetate in heptane) to yield 1.04 g of the amide product (76%).

$^1$H NMR (400 MHz, CHLOROFORM-d) δ ppm 3.07 (qd, J=10.31, 2.25 Hz, 2 H), 4.27-4.34 (m, 1 H), 4.36-4.47 (m, 2 H), 4.57 (dd, J=9.03, 1.22 Hz, 1 H), 5.13 (s, 2 H), 7.30 (d, J=8.10 Hz, 1 H), 7.40 (d, J=0.98 Hz, 1 H), 7.51-7.58 (m, 1 H); LC/MS, 350.0 [M+H]$^+$.

Example 2

1-(3,5-dichloro-4-fluorophenyl)-2,2,2-trifluoroethan-1-one (Intermediate Compound 9)

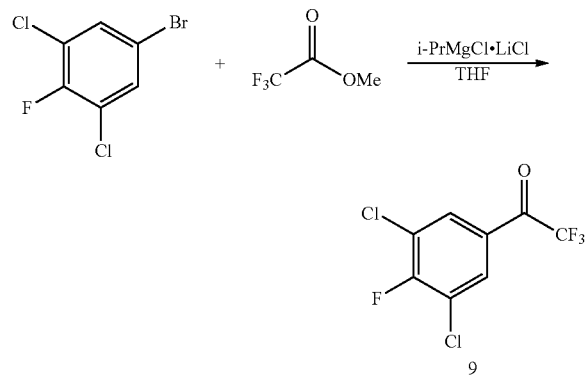

To a cooled (10° C.) solution of 1-bromo-3,5-dichloro-4-fluorobenzene (1.10 kg, 4.51 mol) in THF (9.70 L) was added i-PrMgCl·LiCl (3.64 L, 4.74 mol, 1.3 molar) while maintaining the internal temperature at <20° C. The reaction was stirred for 2 hours with an internal temperature of 18° C., before cooling to −9° C. Methyl trifluoroacetate (499 mL, 4.96 mol) was added while maintaining the internal temperature <10° C. Reaction was warmed to 20° C. and stirred for 3 hours before it was quenched with 4 molar HCl (1.50 L). The biphasic mixture was stirred 2 hours before it was diluted with heptane (4 L). The reaction was mixed for 10 min. and the layers allowed to separate. The aqueous layer was removed extracted 1×2 L EtOAc and the combined organic fractions were washed 1×4 L 22% aq. NaCl and dried over MgSO$_4$ (1.5 kg) for 15 hours. The organic solution was filtered and concentrated in vacuo. The residue was dissolved in toluene (4 L) and concentrated in vacuo. The resultant oil was dissolved in toluene (4 L) and concentrated in vacuo a second time to give 1.06 kg of 1-(3,5-dichloro-4-fluorophenyl)-2,2,2-trifluoroethan-1-one (89%) that was 91% pure.

Note that the yields for smaller scale reactions have ranged between 60-94% for this experiment.

$^1$H NMR (400 MHz, CHLOROFORM-d) δ=8.06 (dd, J=0.8, 6.1 Hz, 2H).

Note that the hemiacetal hydrate can be detected in the $^1$H NMR as a doublet at δ=7.69.

Example 3A 1-(6-Acetylspiro[1H-isobenzofuran-3,3'-azetidine]-1'-yl)-3,3,3-trifluoro-propan-1-one

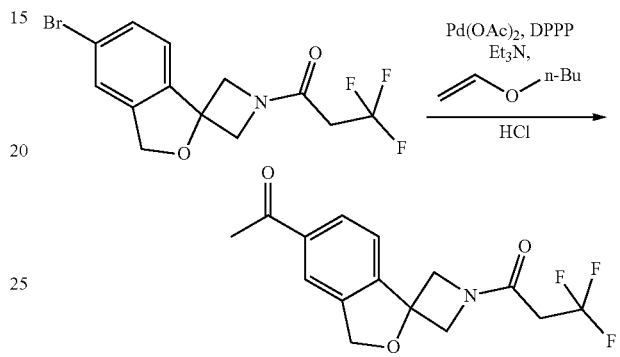

To a 500 mL 1-necked round bottomed flask equipped with a water-cooled condenser atop a Vigreaux (fractionating) column was added 1-(6-bromospiro[1H-isobenzofuran-3,3'-azetidine]-1'-yl)-3,3,3-trifluoro-propan-1-one (4.2 g, 12 mmol). Absolute EtOH (100 mL) was added, and N$_2$ was bubbled through the solution for 30 minutes with stirring. To the resulting solution was added 1,3-bis(diphenylphosphino)propane (0.54 g, 2.4 mmol), Pd(OAc)$_2$ (0.98 g, 2.4 mmol), TEA (5.0 mL,) and butyl vinyl ether (6.0 mL). The flask was placed in a 96° C. preheated oil-bath and stirred at this temperature overnight. Upon cooling, the mixture was quenched with 1N HCl (pH 2-3), then stirred for 2 h at RT and extracted with EtOAc (2×150 mL). The organic layer was washed with water, brine, dried (Na$_2$SO$_4$), filtered and concentrated in vacuo. The crude was loaded on celite and purified on silica gel using heptane/ethyl acetate as eluent to give a white solid. Yield 2.4 g (65%). LCMS (M+H) 314;

$^1$H NMR (400 MHz, DICHLOROMETHANE-d2) δ ppm 2.60 (s, 3 H) 3.08 (qd, J=10.47, 2.76 Hz, 2 H) 4.26-4.33 (m, 1 H) 4.35-4.44 (m, 2 H) 4.56 (d, J=9.27 Hz, 1 H) 5.18 (s, 2 H) 7.54 (d, J=8.00 Hz, 1 H) 7.83 (s, 1 H) 8.00 (dd, J=7.98, 0.76 Hz, 1 H).

3-(3,5-Dichloro-4-fluoro-phenyl)-4,4,4-trifluoro-1-[1'-(3,3,3-trifluoropropanoyl)spiro[3H-isobenzofuran-1,3'-azetidine]-5-yl]but-2-en-1-one

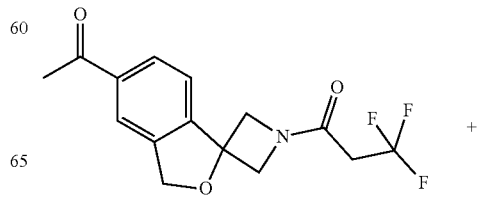

-continued

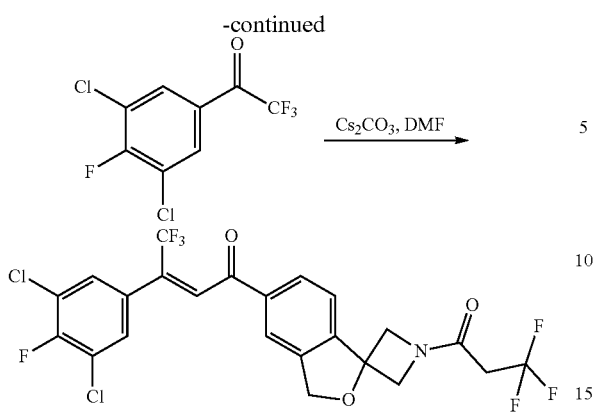

1-(6-Acetylspiro[1H-isobenzofuran-3,3'-azetidine]-1'-yl)-3,3,3-trifluoro-propan-1-one (1.0 g, 3.19 mmol) was taken with 1-(3,5-dichloro-4-fluoro-phenyl)-2,2,2-trifluoro-ethanone (1.25 g, 4.79 mmol) in dry dimethylformamide (DMF) (15 mL). $Cs_2CO_3$ (3.1 g, 9.57 mmol) was added to this and the reaction mixture was stirred for 1 h. The solution filtered and the solid was washed with ethyl acetate (20 mL). The organic mixture was concentrated under vacuum and the crude was dissolved in ethyl acetate (100 mL) and washed with water (20 mL), brine (20 mL) and dried over anhydrous MgSO4, filtered and concentrated. The crude was loaded onto celite and purified on silica gel using heptane/ethyl acetate to give light yellow solid. Yield 1.0 g, 56%. LCMS (M+H) 556;

$^1$H NMR (400 MHz, DICHLOROMETHANE-d2) δ ppm 2.95-3.13 (m, 2 H) 4.17-4.31 (m, 1 H) 4.38 (d, J=10.20 Hz, 2 H) 4.56 (d, J=9.23 Hz, 1H) 5.30-5.36 (m, 2 H) 7.28 (d, J=6.20 Hz, 2 H) 7.45 (d, J=1.37 Hz, 1 H) 7.52-7.56 (m, 1 H) 7.71 (s, 1 H) 7.80-7.91 (m, 1 H).

3-(3,5-Dichloro-4-fluoro-phenyl)-4,4,4-trifluoro-3-sulfanyl-1-[1'-(3,3,3-trifluoropropanoyl)spiro[3H-isobenzofuran-1,3'-azetidine]-5-yl]butan-1-one

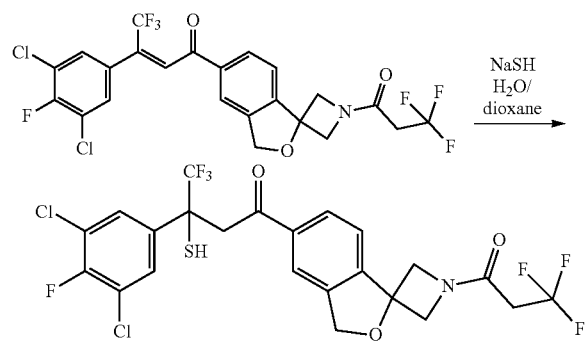

3-(3,5-Dichloro-4-fluoro-phenyl)-4,4,4-trifluoro-1-[1'-(3,3,3-trifluoropropanoyl)spiro[3H-isobenzofuran-1,3'-azetidine]-5-yl]but-2-en-1-one (0.7 g, 1.25 mmol) was dissolved in dioxane (10 mL). NaSH (0.21 g, 3.77 mmol) in water (2 mL) was added to this and the reaction was stirred for 0.5h Reaction was diluted with EtOAc (50 mL) and washed with 1N HCl (10 mL), brine (20 mL) and dried over $Na_2SO_4$. Mixture was filtered and concentrated in vacuo to give 0.65 g of 3-(3,5-dichloro-4-fluoro-phenyl)-4,4,4-trifluoro-3-sulfanyl-1-[1'-(3,3,3-trifluoropropanoyl)spiro[3H-isobenzofuran-1,3'-azetidine]-5-yl]butan-1-one as an off-white solid. (M+H) 590.

$^1$H NMR (400 MHz, DICHLOROMETHANE-d2) δ ppm 3.08 (dd, J=10.37, 2.81 Hz, 2 H) 4.22-4.65 (m, 6 H) 5.18 (s, 2 H) 7.57 (d, J=8.00 Hz, 1H) 7.67 (d, J=6.05 Hz, 2 H) 7.80 (s, 1 H) 7.98 (d, J=8.00 Hz, 1 H).

1-[6-[5-(3,5-Dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one

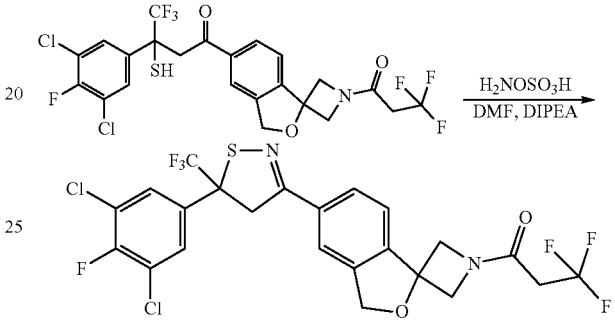

3-(3,5-Dichloro-4-fluoro-phenyl)-4,4,4-trifluoro-3-sulfanyl-1-[1'-(3,3,3-trifluoropropanoyl)spiro[3H-isobenzofuran-1,3'-azetidine]-5-yl]butan-1-one (0.59 g, 1.0 mmol) was taken up in DMF (3.0 mL) and diisopropylethylamine (DIPEA) (0.7 mL) was added to this under nitrogen at room temperature. Hydroxylamine-O-sulfonic acid (0.17 g, 1.5 mmol) was added to this and the reaction was stirred for 30 min. TLC indicated disappearance of starting material and formation of product along with 3-(3,5-dichloro-4-fluoro-phenyl)-4,4,4-trifluoro-1-[1'-(3,3,3-trifluoropropanoyl)spiro[3H-isobenzofuran-1,3'-azetidine]-5-yl]but-2-en-1-one. Reaction was quenched with a saturated LiCl solution (2 mL) and extracted with ethyl acetate (2×20 mL) and organic layer was washed with brine (5 mL), dried over $Na_2SO_4$ and concentrated. The crude was loaded onto celite using DCM and purified on silica gel using heptane/ethyl acetate to give desired product 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one. Yield 123 mg. 21%.

$^1$H NMR (400 MHz, CHLOROFORM-d) δ ppm 1.49 (s, 9 H) 3.88 (d, J=17.47 Hz, 1 H) 4.13-4.16 (m, 2 H) 4.23 (d, J=17.52 Hz, 1 H) 4.34 (d, J=9.91 Hz, 2 H) 5.14 (s, 2 H) 7.39 (d, J=5.91 Hz, 2 H) 7.53 (d, J=7.95 Hz, 1 H) 7.65 (s, 1 H) 7.75 (d, J=8.05 Hz, 1 H).

Example 3B

An alternative method to making 1-[6-[5-(3,5-Dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one, which may also be referred to as 1-(5'-(5-(3,5-dichloro-4-fluorophenyl)-5-(trifluoromethyl)-4,5-dihydroisothiazol-3-yl)-3'H-spiro[azetidine-3,1'-isobenzofuran]-1-yl)-3,3,3-trifluoropropan-1-one depending on naming convention, may be used.

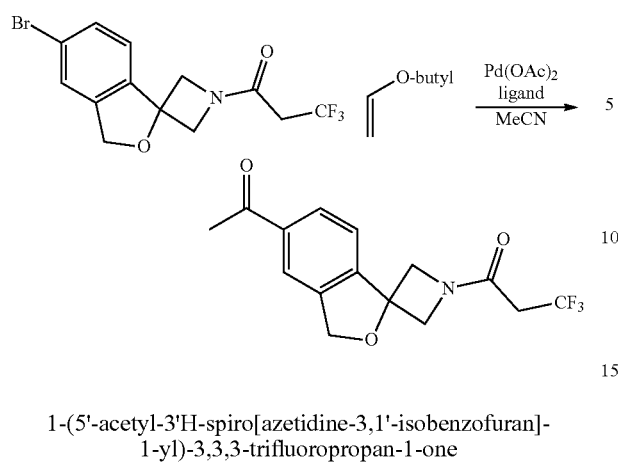
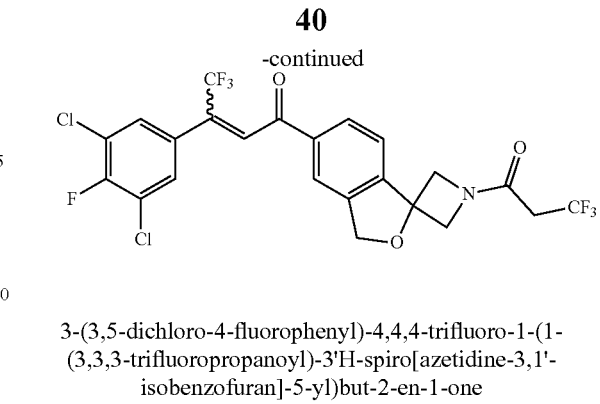

3-(3,5-dichloro-4-fluorophenyl)-4,4,4-trifluoro-1-(1-(3,3,3-trifluoropropanoyl)-3'H-spiro[azetidine-3,1'-isobenzofuran]-5-yl)but-2-en-1-one 1-(5'-acetyl-3'H-spiro[azetidine-3,1'-isobenzofuran]-1-yl)-3,3,3-trifluoropropan-1-one MeCN (7.71 L) was degassed by vigorous bubbling with $N_2$ for 1 h. Pd(OAc)$_2$ (18.5 g, 82.4 mmol) and tri(o-tolyl)phosphine (168 g, 551 mmol) were added and degassing was continued for an additional ½ hour. Triethylamine (1.54 L, 11.0 mol) was added and degassing was continued for an additional ½ hour. Degassing was discontinued and Intermediate Compound 1 (964 g, 2.75 mol) and butyl vinyl ether (2.14 L, 16.5 mol) were added. Reaction was heated to 80° C. for 16 hours under an atmosphere of $N_2$ before quenching with 10% aq HCl (7.00 L). The acidic solution was stirred for 1 hour at room temperature, diluted with EtOAc (8.00 L) and stirred for 15 min. The layers were allowed to separate and the aq. layer was removed and extracted 1×4 L EtOAc. The combined organic fractions were washed 2×4 L 5% aq NaHCO$_3$ and 1×3.5 L 22% aq. NaCl. The organic layer was dried with MgSO$_4$, filtered and concentrated in vacuo. The crude residue (1 kg) was purified on a 5 kg Biotage silica gel column (equilibrated with 16 L heptane). Gradients used for chromatography were: 16 L of 10% EtOAc/heptane, 16 L of 25% EtOAc/heptane, 37 L of 35% EtOAc/heptane, 22 L of 45% EtOAc/heptane, 18 L of 55% EtOAc/heptane and 23 L of 65% EtOAc/heptane. Fractions with R$_f$ 0.18 in 50% EtOAc/heptane were combined and concentrated in vacuo to give 455 g of 1-(5'-acetyl-3'H-spiro[azetidine-3,1'-isobenzofuran]-1-yl)-3,3,3-trifluoropropan-1-one (53%).

Note that the yields for smaller scale reactions have ranged between 50-65% for this experiment.

$^1$H NMR (400 MHz, CHLOROFORM-d) δ=8.01 (d, J=8.0 Hz, 1H), 7.85 (s, 1H), 7.52 (d, J=8.0 Hz, 1H), 5.20 (s, 2H), 4.60 (d, J=9.5 Hz, 1H), 4.49-4.40 (m, 2H), 4.38-4.30 (m, 1H), 3.14-3.02 (m, 2H), 2.64 (s, 3H).

Sodium hydride (45.3 g, 60% in mineral oil, 1.89 mol) was slowly added to a cooled (0° C.) solution of 1-(5'-acetyl-3'H-spiro[azetidine-3,1'-isobenzofuran]-1-yl)-3,3,3-trifluoropropan-1-one (455 g, 1.45 mol) in DMF (5.0 L). The reaction was warmed and maintained at 25° C. for 45 min. before 9 (1.14 kg, 4.36 mol) was added over 10 min. After 30 min., no 1-(5'-acetyl-3'H-spiro[azetidine-3,1'-isobenzofuran]-1-yl)-3,3,3-trifluoropropan-1-one or alcohol intermediate was detected by LCMS and reaction was slowly quenched with water (10 L). Reaction was diluted with EtOAc (8.0 L) and layers were mixed and separated. The aq. layer was extracted with EtOAc (4 L) and the combined organic fractions were washed 2×4 L water and 1×4 L 22% brine. The organic fraction was dried with MgSO$_4$, filtered and concentrated in vacuo to give 1.50 kg of an oil. The oil was chromatographed over silica gel (Biotage 5 kg silica cartridge, eluted with 10 L of 100% heptane, 8.4 L of 5% EtOAc in heptane, 35.6 L of 10% EtOAc in heptane, 18.8 L of 15% EtOAc in heptane, 20 L of 20% EtOAc in heptane, 16 L of 25% EtOAc in heptane, 17.1 L of 30% EtOAc in heptane, 18.5 L of 35% EtOAc in heptane, 13.7 L of 40% EtOAc in heptane and 14.5 L of 45% EtOAc in heptane) to give 593 g of 3-(3,5-dichloro-4-fluorophenyl)-4,4,4-trifluoro-1-(1-(3,3,3-trifluoropropanoyl)-3'H-spiro[azetidine-3,1'-isobenzofuran]-5-yl)but-2-en-1-one (73%).

Note that yields for smaller scale reactions have ranged between 60-75% for this experiment.

$^1$H NMR (400 MHz, CHLOROFORM-d) δ=7.88 (dd, J=0.6, 8.0 Hz, 1H), 7.72 (s, 1H), 7.53 (d, J=8.0 Hz, 1H), 7.41 (d, J=1.2 Hz, 1H), 7.24 (d, J=6.1 Hz, 2H), 5.18 (s, 2H), 4.61 (d, J=9.1 Hz, 1H), 4.48-4.39 (m, 2H), 4.35-4.30 (m, 1H), 3.14-3.02 (m, 2H).

Note that a mixture in the range between 80:20 and 85:15 of enone isomers are typically generated for this experiment. The major enone conformation is unknown at this time.

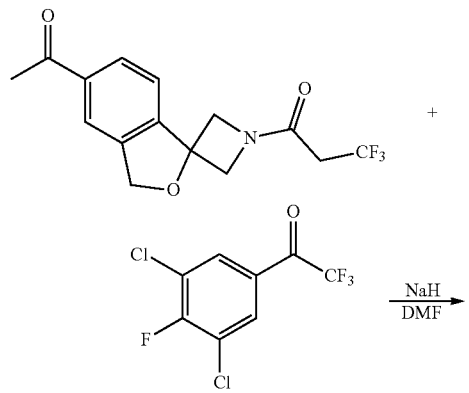
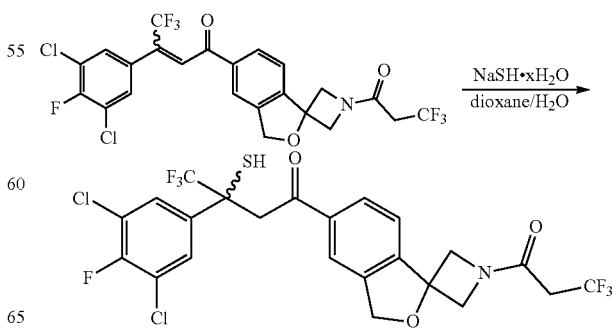

3-(3,5-dichloro-4-fluorophenyl)-4,4,4-trifluoro-3-mercapto-1-(1-(3,3,3-trifluoropropanoyl)-3'H-spiro[azetidine-3,1'-isobenzofuran]-5-yl)butan-1-one A solution of 3-(3,5-dichloro-4-fluorophenyl)-4,4,4-trifluoro-1-(1-(3,3,3-trifluoropropanoyl)-3'H-spiro[azetidine-3,1'-isobenzofuran]-5-yl)but-2-en-1-one (593 g, 1.07 mol) and water (2.43 L) in dioxane (10.7 L) was degassed by sparging with $N_2$ for 1 hour. Crushed NaSH.x$H_2$O (0.600 kg, 8.10 mol) added and reaction was stirred at room temperature for 2 hours. The reaction was diluted with EtOAc (10.7 L) and quenched with aq. HCl (10.9 L, 1 molar). The phases were separated and the organic fraction was washed 1×5.4 L aq. HCl (1 molar). The combined aq. layers were extracted 1×2 L EtOAc, and the combined organic fractions were washed 1×5.4 L 22% brine. The organic fraction was dried with $MgSO_4$, filtered and concentrated in vacuo to give a solid foam. The foam was dried in a vac. oven (45° C.) for 18 hours to give 590 g of 3-(3,5-dichloro-4-fluorophenyl)-4,4,4-trifluoro-3-mercapto-1-(1-(3,3,3-trifluoropropanoyl)-3'H-spiro[azetidine-3,1'-isobenzofuran]-5-yl)butan-1-one (quantitative).

$^1$H NMR (400 MHz, CHLOROFORM-d) δ=7.99 (d, J=8.0 Hz, 1H), 7.81 (s, 1H), 7.63 (d, J=6.0 Hz, 2H), 7.56 (d, J=8.0 Hz, 1H), 5.20 (s, 2H), 4.62 (d, J=9.0 Hz, 1H), 4.50-4.39 (m, 2H), 4.38-4.24 (m, 2H), 3.99 (d, J=18.4 Hz, 1H), 3.30 (s, 1H), 3.09 (dq, J=2.4, 10.3 Hz, 2H)

1-(5'-(5-(3,5-dichloro-4-fluorophenyl)-5-(trifluoromethyl)-4,5-dihydroisothiazol-3-yl)-3'H-spiro[azetidine-3,1'-isobenzofuran]-1-yl)-3,3,3-trifluoropropan-1-one To a cooled (−50° C.) solution of 3-(3,5-dichloro-4-fluorophenyl)-4,4,4-trifluoro-3-mercapto-1-(1-(3,3,3-trifluoropropanoyl)-3'H-spiro[azetidine-3,1'-isobenzofuran]-5-yl)butan-1-one (433 g, 733 mmol) in THF (8.66 L) was added hydroxylamine-O-sulfonic acid (166 g, 1.47 mol). A pre-cooled (−50° C.) solution of KOH in MeOH (9.17 L, 0.30 molar. 2.75 mol) was added at a rate of 0.3 L/min. After KOH addition, the reaction was allowed to slowly warm to 0° C. over 2h. Reaction was quenched with aq. HCl (9 L, 1 molar), diluted with EtOAc (9 L) and heptanes (4 L) and stirred for 10 min. Biphasic mixture was separated and the aqueous layer was extracted 2×13.5 L 2:1 EtOAc/heptanes. The combined organic fractions were washed 1×4 L 22% brine and concentrated in vacuo to give 480 g of crude material. The resultant residue was split in half and each half was chromatographed on silica gel (5 kg Silicycle silica gel cartridge, eluted with 5 L heptanes, 8.4 L of 5% EtOAc in heptanes, 21 L of 10% EtOAc in heptanes, 22 L of 15% EtOAc in heptanes, 24 L of 20% EtOAc in heptanes and 20 L of 23% EtOAc in heptanes) to give 0.200 kg of SCY-344 (46%).

$^1$H NMR (400 MHz, CHLOROFORM-d) δ=7.77 (dd, J=4.1, 8.0 Hz, 1H), 7.69 (d, J=4.8 Hz, 1H), 7.48 (d, J=8.0 Hz, 1H), 7.39 (d, J=5.9 Hz, 2H), 5.18 (s, 2H), 4.60 (d, J=9.1 Hz, 1H), 4.49-4.39 (m, 2H), 4.37-4.31 (m, 1H), 4.23 (d, J=17.5 Hz, 1H), 3.88 (d, J=17.4 Hz, 1H), 3.08 (dq, J=2.2, 10.3 Hz, 2H).

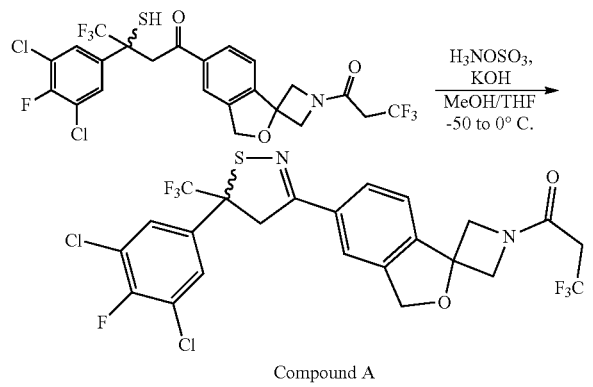

Compound A

Example 4 Chiral Separation

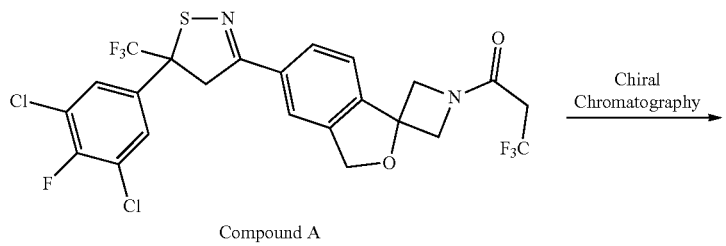

Compound A

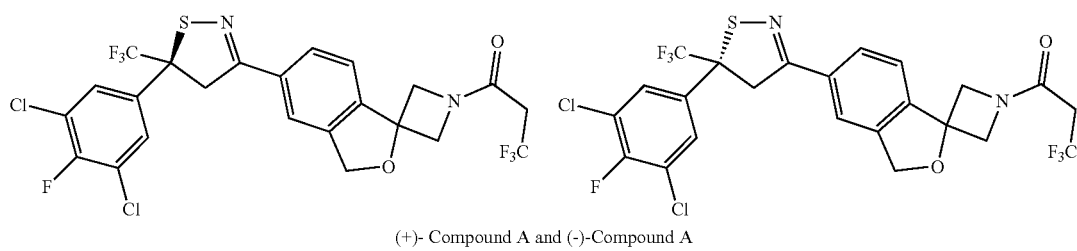

(+)- Compound A and (−)-Compound A

43

Isomers of Compound A: (+)-Compound A and (−)-Compound A

Racemic Compound A consisting of both (+) and (−) enantiomers was dissolved in methyl t-butyl ether (MTBE) at a concentration of 30 mg/mL. The solution was filtered through a 0.2 μm PTFE filter with vacuum. The filtrate was purified on a Gilson Preparative HPLC system controlled by Gilson UniPoint software and consisting of a 215 liquid handler, an 849 injector, a 156 UV detector, and a 322 HPLC pump. The preparative HPLC column used was a Chiralpak IC, 21×150 mm, 5 μm and was heated by a Timberline TL-105 column heater to 40° C. The enantiomeric peaks were separated under isocratic conditions which are summarized in Table 1 below.

TABLE 1

| HPLC conditions | |
| --- | --- |
| Column | Chiralpak IC, 21 × 150 mm, 5 μm |
| Column Temperature | 40° C. |
| Sample Temperature | Ambient |
| Flow Rate | 30 mL/min |
| Run Time | 10 minutes |
| Injection Volume | 1000 μL |
| Detection | UV at 270 nm |
| Isocratic Mobile Phase | 66:30:4 MTBE/Heptanes/Isopropanol |
| Diluent | MTBE |

Both isomer peaks ((+) and (−)) were collected and concentrated to dryness using rotary evaporation at 20° C. and then further dried under high vacuum to form a solid. In order to remove solvents from the isolates, the materials were then dried under high vacuum at 45° C. for 3 days.

Example 5 Chiral Synthesis

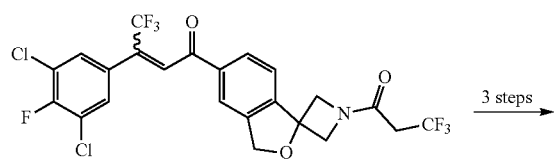

3 steps →

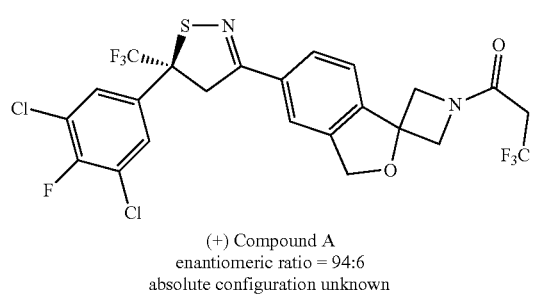

(+) Compound A
enantiomeric ratio = 94:6
absolute configuration unknown 1-(5'-(5-(3,5-dichloro-4-fluorophenyl)-5-(trifluoromethyl)-4,5-dihydroisothiazol-3-yl)-3'H-spiro[azetidine-3,1'-isobenzofuran]-1-yl)-3,3,3-trifluoropropan-1-one

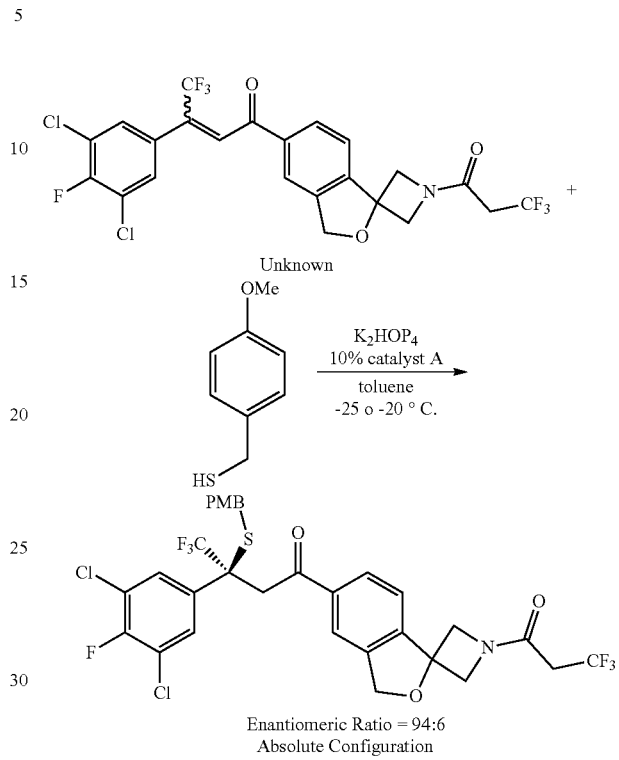

Enantiomeric Ratio = 94:6
Absolute Configuration 3-(3,5-dichloro-4-fluorophenyl)-4,4,4-trifluoro-3-((4-methoxybenzyl)thio)-1-(1-(3,3,3-trifluoropropanoyl)-3'H-spiro[azetidine-3,1'-isobenzofuran]-5-yl)butan-1-one To a cooled (−20° C.) solution of 3-(3,5-dichloro-4-fluorophenyl)-4,4,4-trifluoro-1-(1-(3,3,3-trifluoropropanoyl)-3'H-spiro[azetidine-3,1'-isobenzofuran]-5'-yl)but-2-en-1-one (3.00 g, 5.39 mmol) in toluene (22 mL) was added 3-[[3,5-Bis(trifluoromethyl)phenyl]amino]-4-[[(8α,9S)-6'-methoxycinchonan-9-yl]amino]-3-cyclobutene-1,2-dione (referred to as Catalyst A, 0.340 g, 0.539 mmol) and K$_2$HPO$_4$ (1.88 g, 10.8 mmol). Reaction maintained at −20° C. for 15 min. before PMB thiol (3.76 mL, 27.0 mmol) was added dropwise over 10 min. Reaction was maintained at −20° C. for ~19 h then filtered through a Buchner funnel. Solids were rinsed with toluene (5 mL) and combined solutions were concentrated in vacuo. The residue was chromatographed twice over silica gel (Isco 120 gram gold silica cartridge, gradient 0 to 40% EtOAc in heptanes over 45 min) to give 2.99 g of 3-(3,5-dichloro-4-fluorophenyl)-4,4,4-trifluoro-3-((4-methoxybenzyl)thio)-1-(1-(3,3,3-trifluoropropanoyl)-3'H-spiro[azetidine-3,1'-isobenzofuran]-5'-yl)butan-1-one (78%).

Note that the absolute configuration of major isomer is currently unknown.

$^1$H NMR (400 MHz, CHLOROFORM-d) δ=7.84 (t, J=6.8 Hz, 1H), 7.66 (s, 1H), 7.58 (d, J=6.0 Hz, 2H), 7.48 (dd, J=1.9, 8.0 Hz, 1H), 7.10 (d, J=8.7 Hz, 2H), 6.76 (d, J=8.6 Hz, 2H), 5.17 (s, 2H), 4.61 (d, J=8.9 Hz, 1H), 4.49-4.39 (m, 2H), 4.37-4.30 (m, 1H), 3.94-3.88 (m, 1H), 3.85 (d, J=12.0 Hz, 1H), 3.79-3.70 (m, 4H), 3.65 (d, J=12.0 Hz, 1H), 3.08 (dq, J=2.5, 10.3 Hz, 2H).

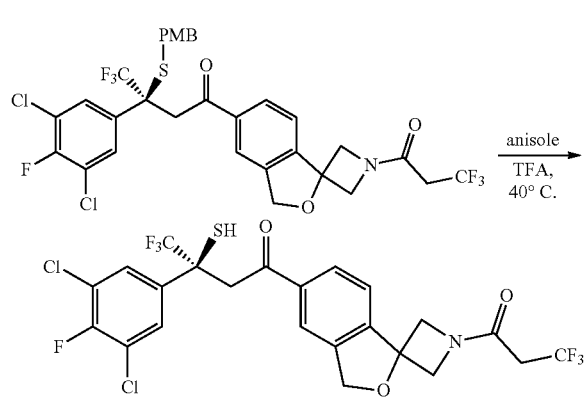

3-(3,5-dichloro-4-fluorophenyl)-4,4,4-trifluoro-3-mercapto-1-(1-(3,3,3-trifluoropropanoyl)-3'H-spiro[azetidine-3,1'-isobenzofuran]-5-yl)butan-1-one To a solution of 3-(3,5-dichloro-4-fluorophenyl)-4,4,4-trifluoro-3-((4-methoxybenzyl)thio)-1-(1-(3,3,3-trifluoropropanoyl)-3'H-spiro[azetidine-3,1'-isobenzofuran]-5'-yl)butan-1-one (1.48 g, 2.08 mmol) in anisole (1.58 mL, 14.6 mmol) was added TFA (21.0 mL). Reaction was heated 40° C. for 5 h. before it was quenched by slowly pouring into a 3:2 mixture of saturated aq. NaHCO₃/EtOAc (500 mL) with stirring. Stirring was continued until no gas evolution was observed. The aq layer was separated and the organic layer was washed 2×25 mL NaHCO₃, 1×50 mL saturated aq NaCl. The organic layer was dried over Na₂SO₄, filtered concentrated in vacuo to give a brown oil. The oil was chromatographed on silica gel (Isco 120 gram gold silica cartridge, gradient 0 to 50% EtOAc in heptanes over 45 min) to give 0.840 g of contaminated 3-(3,5-dichloro-4-fluorophenyl)-4,4,4-trifluoro-3-mercapto-1-(1-(3,3,3-trifluoropropanoyl)-3'H-spiro[azetidine-3,1'-isobenzofuran]-5-yl)butan-1-one (~61%), (90% pure by ¹H NMR).

¹H NMR (400 MHz, CHLOROFORM-d) δ=7.99 (d, J=8.2 Hz, 1H), 7.81 (d, J=0.6 Hz, 1H), 7.63 (d, J=6.0 Hz, 2H), 7.56 (d, J=8.0 Hz, 1H), 5.21 (s, 2H), 4.62 (d, J=8.5 Hz, 1H), 4.49-4.42 (m, 2H), 4.37-4.33 (m, 1H), 4.28 (d, J=18.4 Hz, 1H), 3.99 (d, J=18.4 Hz, 1H), 3.30 (s, 1H), 3.09 (dq, J=2.5, 10.3 Hz, 2H).

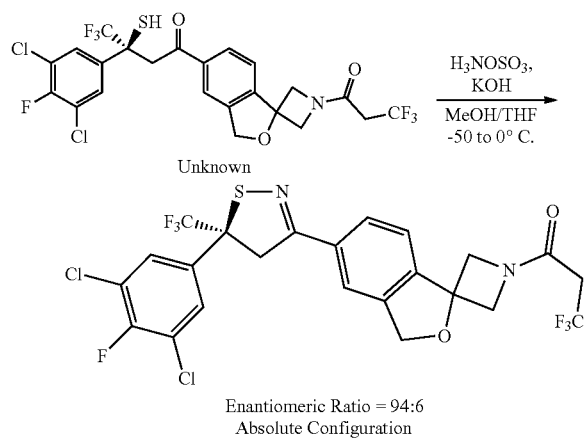

Enantiomeric Ratio = 94:6
Absolute Configuration (+) Compound A

To a cooled (−50° C.) solution of 3-(3,5-dichloro-4-fluorophenyl)-4,4,4-trifluoro-3-mercapto-1-(1-(3,3,3-trifluoropropanoyl)-3'H-spiro[azetidine-3,1'-isobenzofuran]-5-yl)butan-1-one (0.810 g, 1.37 mmol) in THF (17 mL) was added hydroxylamine-O-sulfonic acid (0.310 g, 2.74 mmol). A solution of KOH in MeOH (8.60 mL, 0.60 molar) was added dropwise over 14 min. so that the internal temperature was <−40° C. After KOH addition, the reaction was allowed to slowly warm to −2° C. over 2h. Reaction was quenched with 10% HCl (17 mL), diluted with EtOAc (17 mL) and stirred for 10 min. Biphasic mixture was diluted with heptanes (9 mL) mixed and the layers separated. The aqueous layer was extracted 1×10 mL EtOAc and the combined organic fractions were washed 2×10 mL sat. aq. NaHCO₃, 1×10 mL saturated aq. NaCl, dried over Na₂SO₄, filtered and concentrated in vacuo. The resultant residue was chromatographed on silica gel (Isco 120 gram gold silica cartridge, gradient 0 to 45% EtOAc in heptanes over 45 min) to give 191 mg of (+) Compound A (24%).

Note that the absolute configuration of major isomer is currently unknown. Enantiomeric ratio was determined to be 94:6 by chiral HPLC.

¹H NMR (400 MHz, CHLOROFORM-d) δ=7.77 (dd, J=4.1, 8.0 Hz, 1H), 7.69 (d, J=4.8 Hz, 1H), 7.48 (d, J=8.0 Hz, 1H), 7.39 (d, J=5.9 Hz, 2H), 5.18 (s, 2H), 4.60 (d, J=9.1 Hz, 1H), 4.49-4.39 (m, 2H), 4.37-4.31 (m, 1H), 4.23 (d, J=17.5 Hz, 1H), 3.88 (d, J=17.4 Hz, 1H), 3.08 (dq, J=2.2, 10.3 Hz, 2H).

All publications, patents and patent applications cited in this specification are incorporated herein by reference for the teaching to which such citation is used.

The specific responses observed may vary according to and depending on the particular active compound selected or whether there are present carriers, as well as the type of formulation and mode of administration employed, and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

The invention claimed is:

1. A compound 1-(6-bromospiro[1H-isobenzofuran-3,3'azetidine]-1'-yl)-3,3,3-trifluoro-propane-1-one.

2. A process for making 1-[6-[5-(3,5-dichloro-4-fluorophenyl)-5-(trifluoromethyl)-4H-isothiazol-3-yl]spiro[1H-isobenzofuran-3,3'-azetidine]-1'-yl]-3,3,3-trifluoro-propan-1-one or a salt thereof comprising using 1-(6-bromospiro[1H-isobenzofuran-3,3'azetidine]-1'-yl)-3,3,3-trifluoro-propane-1-one.

3. A process for making 1-(6-bromospiro[1H-isobenzofuran-3,3'azetidine]-1'-yl)-3,3,3-trifluoro-propane-1-one comprising:
   a) acylating an azetidinone or a salt thereof with 3,3,3-trifluoroprionyl chloride;
   and
   b) spirocyclizing using 4-bromo-2-(chloromethyl)-1-iodo-benzene.

4. A process for making 1-(6-bromospiro[1H-isobenzofuran-3,3'azetidine]-1'-yl)-3,3,3-trifluoro-propane-1-one comprising:

a) protecting azetidinone hydrochloride with a protecting group;
b) spirocyclizing;
c) removing the protecting group; and
d) acylating using 3,3,3-trifluoroprionyl chloride.

5. The process of claim 4, wherein the spirocyclizing step uses 4-bromo-2-(chloromethyl)-1-iodo-benzene.

6. The process of claim 3, wherein the spirocyclizing step further comprises an anhydrous lanthanide salt.

7. The process of claim 4, wherein the spirocyclizing step further comprises an anhydrous lanthanide salt.

8. The process of claim 6, wherein a dioxaneone is used to spirocyclize 4-bromo-2-(chloromethyl)-1-iodo-benzene, followed by opening the dioxane ring to a di-alcohol, converting to a di-nitrobenzenesulfonate, and subsequently closing the ring to form an spiroazetidine moiety.

9. A compound 3-(3,5-dichloro-4-fluoro-phenyl)-4,4,4-trifluoro-1-[1'-(3,3,3-trifluoropropanoyl)spiro[3H-isobenzofuran-1,3'-azetidine]-5-yl]but-2-en-1-one.

10. A compound 3-(3,5-dichloro-4-fluoro-phenyl)-4,4,4-trifluoro-3-sulfanyl-1-[1'-(3,3,3-trifluoropropanoyl)spiro[3H-isobenzofuran-1,3'-azetidine]-5-yl]butan-1-one.

11. A process for making 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one or a salt thereof comprising: forming an isothiazoline ring by treating 3-(3,5-dichloro-4-fluoro-phenyl)-4,4,4-trifluoro-3-sulfanyl-1-[1'-(3,3,3-trifluoropropanoyl)spiro[3H-isobenzofuran-1,3'-azetidine]-5-yl]butan-1-one with hydroxylamine-O-sulfonic acid.

12. A process for making 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one or salt thereof comprising using 3-(3,5-dichloro-4-fluoro-phenyl)-4,4,4-trifluoro-1-[1'-(3,3,3-trifluoropropanoyl)spiro[3H-isobenzofuran-1,3'-azetidine]-5-yl]but-2-en-1-one.

13. A process for making 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one or salt thereof comprising using 3-(3,5-dichloro-4-fluoro-phenyl)-4,4,4-trifluoro-3-sulfanyl-1-[1'-(3,3,3-trifluoropropanoyl)spiro[3H-isobenzofuran-1,3'-azetidine]-5-yl]butan-1-one.

14. A process for making 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one or a salt thereof comprising:
  a) converting 1-(6-bromospiro[1H-isobenzofuran-3,3'azetidine]-1'-yl)-3,3,3-trifluoro-propane-1-one to an acetophenone derivative via palladium coupling;
  b) reacting the acetophenone derivative to form an enone derivative;
  c) treating the enone derivative with sodium thiolate to form a sulfanyl derivative; and
  d) reacting the sulfanyl derivative with hydroxylamine-O-sulfonic acid to form 1-[6-[5-(3,5-dichloro-4-fluorophenyl)-5-(trifluoromethyl)-4H-isothiazol-3-yl]spiro[1H-isobenzofuran-3,3'-azetidene]-1'-yl]-3,3,3-trifluor-propan-1-one or salt thereof.

15. The process of claim 14, wherein the reagent of step (b) is 1-(3,5-dichloro-4-fluorophenyl)-2,2,2-trifluoroethan-1-one.

16. A compound of Formula (I)

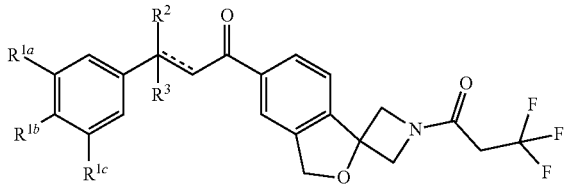

Formula (I)

wherein
each of $R^{1a}$, $R^{1b}$, and $R^{1c}$ individually is a halogen;
$R^2$ is a $C_{1-6}$ haloalkyl;
the depicted dashed bond is absent or present to form a double bond; and
$R^3$ is SH if the depicted dashed bond is absent.

17. The compound of claim 16, wherein
$R^{1a}$ is Cl;
$R^{1b}$ is F; and
$R^{1c}$ is Cl.

18. The compound of claim 16, wherein
$R^2$ is $CF_3$; and
the depicted dashed bond is present to form a double bond; or
the depicted dashed bond is absent; and
$R^3$ is SH.

19. A compound 1-(6-Acetylspiro[1H-isobenzofuran-3,3'-azetidine]-1'-yl)-3,3,3-trifluoro-propan-1-one.

20. A process for making 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one or a salt thereof comprising using 1-(6-Acetylspiro[1H-isobenzofuran-3,3'-azetidine]-1'-yl)-3,3,3-trifluoro-propan-1-one.

* * * * *

UNITED STATES PATENT AND TRADEMARK OFFICE
CERTIFICATE OF CORRECTION

PATENT NO. : 10,556,909 B2
APPLICATION NO. : 16/302944
DATED : February 11, 2020
INVENTOR(S) : Speake et al.

It is certified that error appears in the above-identified patent and that said Letters Patent is hereby corrected as shown below:

In the Claims

Column 46, Line 53, Claim 2, "3,3,3-trifluoro-propan-" should be --3,3,3-trifluoro-propane- --;

Column 47, Line 25, Claim 11, "3,3,3-trifluoro-propan-" should be --3,3,3-trifluoro-propane- --;
Column 47, Line 29, Claim 11, "]butan-1-one with" should be --]butane-1-one with--;

Column 47, Line 40, Claim 12, "3,3,3-trifluoro-propan-" should be --3,3,3-trifluoro-propane- --;
Column 47, Line 44, Claim 12, "]butan-1-one" should be --]butane-1-one--;

Column 47, Line 47, Claim 14, "3,3,3-trifluoro-propan-" should be --3,3,3-trifluoro-propane- --;
Column 48, Line 9, Claim 14, "trifluor-propan-1-one" should be --trifluro-propane-1-one--;

Column 48, Line 43, Claim 19, "tnfluoro-propan-1-one" should be --trifluoro-propane-1-one--;

Column 48, Line 49, Claim 20, "propan-1-one" should be --propane-1-one--.

Signed and Sealed this
Twenty-ninth Day of September, 2020

Andrei Iancu
*Director of the United States Patent and Trademark Office*